United States Patent
Pia

(10) Patent No.: US 12,102,103 B2
(45) Date of Patent: Oct. 1, 2024

(54) ANIMAL FEED COMPOSITIONS AND USES THEREOF

(71) Applicants: Novozymes A/S, Bagsvaerd (DK); DSM IP Assets B.V., Heerlen (NL)

(72) Inventor: Eduardo Antonio Della Pia, Lyngby (DK)

(73) Assignees: Novozymes A/S, Bagsvaerd (DK); DSM IP Assets B.V., Heerlen (NL)

( * ) Notice: Subject to any disclaimer, the term of this patent is extended or adjusted under 35 U.S.C. 154(b) by 150 days.

(21) Appl. No.: 16/960,332

(22) PCT Filed: Jan. 11, 2019

(86) PCT No.: PCT/EP2019/050610
§ 371 (c)(1),
(2) Date: Jul. 7, 2020

(87) PCT Pub. No.: WO2019/138024
PCT Pub. Date: Jul. 18, 2019

(65) Prior Publication Data
US 2021/0227853 A1    Jul. 29, 2021

(30) Foreign Application Priority Data
Jan. 11, 2018    (EP) .................................... 18151256

(51) Int. Cl.
| A23K 20/189 | (2016.01) |
| A23K 10/14 | (2016.01) |
| A23K 20/22 | (2016.01) |
| A23K 20/24 | (2016.01) |

(52) U.S. Cl.
CPC ............ *A23K 20/189* (2016.05); *A23K 10/14* (2016.05); *A23K 20/22* (2016.05); *A23K 20/24* (2016.05); *C12Y 302/01008* (2013.01)

(58) Field of Classification Search
CPC ...... A23K 10/14; A23K 20/22; A23K 20/189; A23K 20/24; C12P 19/14; C12P 19/04; C12N 9/2481; C12Y 302/01136; C12Y 302/01032; C12Y 302/01008
See application file for complete search history.

(56) References Cited

U.S. PATENT DOCUMENTS 10,208,301 B2 * 2/2019 Danielsen ................ C12N 5/04

FOREIGN PATENT DOCUMENTS

| CN | 101522045 A | 9/2009 |
| CN | 107072251 A | 8/2017 |
| CN | 111492053 A | 8/2020 |
| WO | 03/106654 A2 | 12/2003 |
| WO | 2008/017661 A1 | 2/2008 |
| WO | 2008037757 A1 | 4/2008 |
| WO | 2016071302 A1 | 5/2016 |
| WO | 2017/103159 A2 | 6/2017 |
| WO | 2018/007154 A1 | 1/2018 |
| WO | 2018/234465 A1 | 12/2018 |
| WO | 2019121930 A1 | 6/2019 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Khandeparker et al., Xylanolytic enzyme systems in Arthrobacter sp. MTCC 5214 and Lactobacillus sp. Biotechnol. Appl. Chem., 2014: 245-254. (Year: 2014).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Wood et al., Dye Interactions, a basis for specific detection and histochemistry of polysaccharides. The J. Histochem. Cytochem., 1983, vol. 31(6): 823-826. (Year: 1983).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Guo et al., Protein tolerance to random amino acid change. PNAS., 2004, vol. 101 (25): 9205-9210. (Year: 2004).*
Maehara et al., GH30 Glucuronoxylan-Specific Xylanase from Streptomyces turgidiscabies C56. Appl. Environ. Microbiol., 2018, vol. 78(11): 3923-3931. (Year: 2018).*
St. John et al., A novel member of glycoside hydrolase family 30 subfamily 8 with altered substrate specificity. Acta Cryst. 2014, D70: 2950-2958. (Year: 2014).*
Suchova et al., Glucuronoxylan recognition by GH 30 xylanases: A study with enzyme and substrate variants. Arch. Biochem. Biophys., 2018, vol. 643: 42-49. (Year: 2018).*
Correia et al., Structure and Function of an Arabinoxylan-specific Xylanase*. The J. Biol. Chem., 2011, vol. 286(25): 22510-22520. (Year: 2011).*
Sainz-Polo et al., Structural Analysis of Glucuronoxylan-specific Xyn30D and Its Attached CBM35 Domain Gives Insights into the Role of Modularity in Specificity*. The J. Biol. Chem., 2014, vol. 289(45): 31088-31101 (Year: 2014).*
Sainz-Polo et al., Structural Analysis of Glucuronoxylan-specific Xyn30D and Its Attached CBM35 Domain Gives Insights into the Role of Modularity in Specificity*. The J. Biol. Chem., 2014, vol. 286(45): 31088-31101. (Year: 2014).*

(Continued)

*Primary Examiner* — Ganapathirama Raghu
(74) *Attorney, Agent, or Firm* — Adam Rucker

(57) ABSTRACT

The presence of either a calcium source or a carbonate source with GH30 xylanses significantly improves the release of xylan oligomers from maize and other feeds compared to the same xylanases without the calcium or carbonate source. Animal feed and animal feed additives comprising a combination of one or more polypeptides having xylanase activity; and one or more sources of calcium; and/or one or more sources of carbonate, wherein the polypeptide is a GH30 xylanase provide for improved xylan release from feedstuff.

20 Claims, 1 Drawing Sheet
Specification includes a Sequence Listing.

(56) References Cited

OTHER PUBLICATIONS

Valenzuela et al., Modular Glucuronoxylan-Specific Xylanase with a Family CBM35 Carbohydrate-Binding Module. Appl. Environ. Microbiol., 2012, vol. 78(11): 3923-3931. (Year: 2012).*
Agger et al, Journal of Agricultural and Food Chemistry, vol. 58, pp. 6141-6148 (2010).
Huisman et al., Carbohydrate Polymers, vol. 43, pp. 269-279 (2000).
Popper et al., Plant Physiology, vol. 153, pp. 373-383 (2010).
Santos et al., Journal of Biological Chemistry, No. 289, No. 46, pp. 32186-32200 (2014).
Liu (ED), 2006, Food Enzymology, 43—Tr.

* cited by examiner

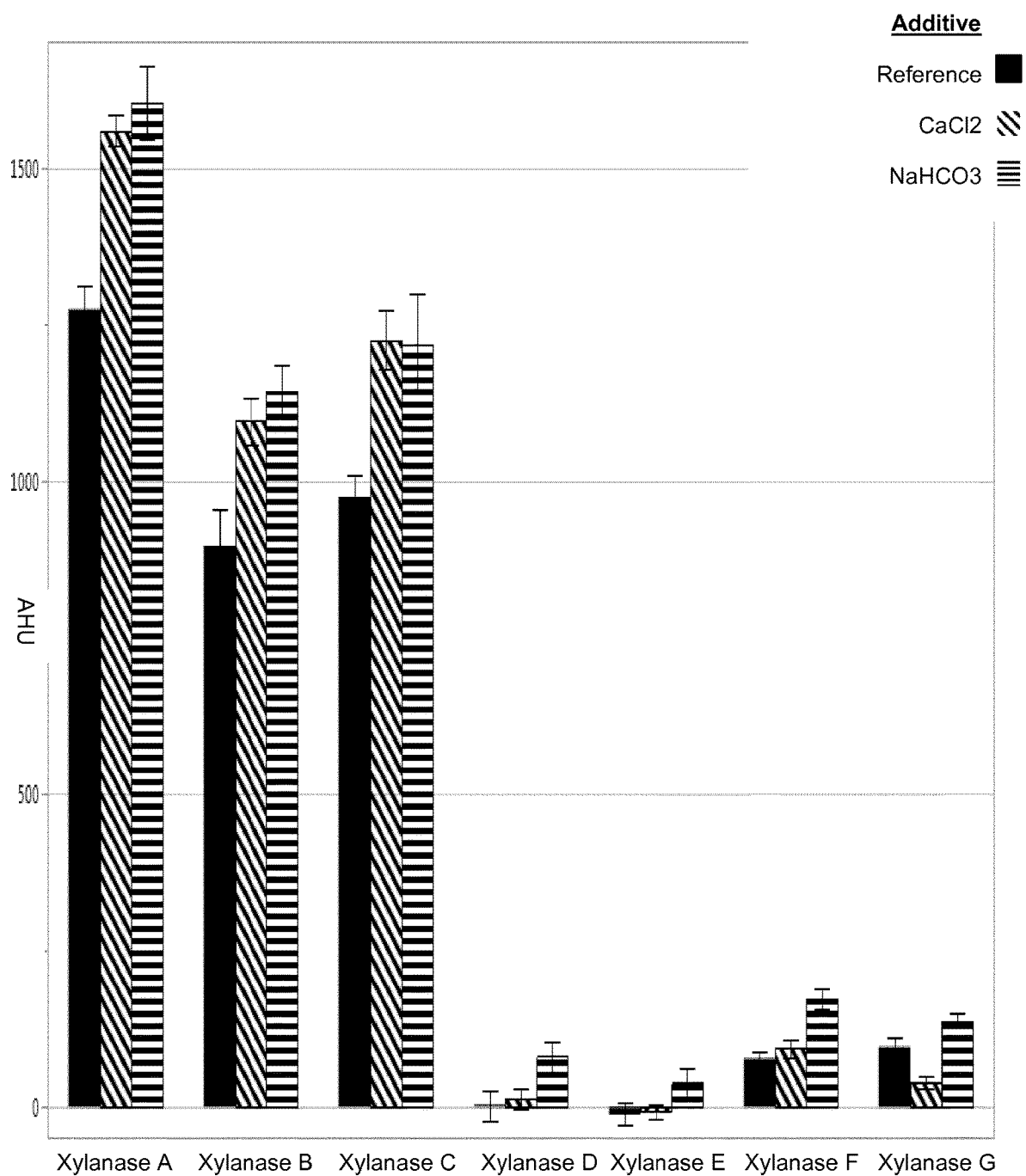

ANIMAL FEED COMPOSITIONS AND USES THEREOF

CROSS-REFERENCE TO RELATED APPLICATIONS

This application is a 35 U.S.C. 371 national application of international application no. PCT/EP2019/050610 filed Jan. 11, 2019, which claims priority or the benefit under 35 U.S.C. 119 of European application no. 18151256.7 filed Jan. 11, 2018. The content of each application is fully incorporated herein by reference.

REFERENCE TO A SEQUENCE LISTING

This application contains a Sequence Listing in computer readable form, which is incorporated herein by reference. The text file is named sequence.txt, which was created on Aug. 21, 2020 and has 70.5 KB bytes.

FIELD OF THE INVENTION

The present invention relates to an animal feed composition comprising a xylanase together with calcium and/or a carbonate source.

BACKGROUND OF THE INVENTION

Xylans are hemicelluloses found in all land plants (Popper and Tuohy, 2010, *Plant Physiology* 153: 373-383). They are especially abundant in secondary cell walls and xylem cells. In grasses, with type II cell walls, glucurono arabinoxylans are the main hemicellulose and are present as soluble or insoluble dietary fiber in many grass based food and feed products.

Plant xylans have a β-1,4-linked xylopyranose backbone that can be substituted at the O2 or O3 position with arabinose, glucuronic acid and acetic acid in a species and tissue specific manner. The starch-rich seeds of the subfamily Panicoideae with economically important species such as corn, sorghum, rice and millet have special types of highly substituted xylans in their cell walls. Compared to wheat flour, wherein over 60% of the xylosyl units in the arabinoxylan backbone are unsubstituted. In corn kernel xylan, the corresponding percentage of unsubstituted backbone xylosyls is 20-30%, and in sorghum it is 35-40% (Huismann et al., 2000, *Carbohydrate Polymers* 42: 269-279). Furthermore, in corn and sorghum the xylan side chains can be longer than a single arabinose or glucuronic acid substitution which is common in other xylans. This added side chain complexity is often due to L- and D-galactose and D-xylose sugars bound to the side chain arabinose or glucuronic acid. About every tenth arabinose in corn kernel xylan is also esterified with a ferulic acid and about every fourth xylose carries an acetylation (Agger et al., 2010, *J. Agric. Food Chem.* 58: 6141-6148). All of these factors combined make the highly substituted xylans in corn and sorghum resistant to degradation by traditional xylanases.

The known enzymes responsible for the hydrolysis of the xylan backbone are classified into enzyme families based on sequence similarity (cazy.org). The enzymes with mainly endo-xylanase activity have previously been described in Glycoside hydrolase family (GH) 5, 8, 10, 11, 30 and 98. The enzymes within a family share some characteristics such as 3D fold and they usually share the same reaction mechanism. Some GH families have narrow or mono-specific substrate specificities while other families have broad substrate specificities.

Commercially available GH10 and GH11 xylanases are often used to break down the xylose backbone of arabinoxylan. In animal feed this results in a degradation of the cereal cell wall with a subsequent improvement in nutrient release (starch and protein) encapsulated within the cells. Degradation of xylan also results in the formation of xylose oligomers that may be utilised for hind gut fermentation and therefore can help an animal to obtain more digestible energy.

However, such xylanases are sensitive to side chain steric hindrance and whilst they are effective at degrading arabinoxylan from wheat, they are not very effective on the xylan found in the seeds of *Poaceae* species, such as corn or sorghum.

WO03106654 discloses numerous polypeptides with putative xylanase activity. Variants of the GH30 xylanase of SEQ ID NO 190 are described in WO03106654 in order to overcome inherent pH and thermo-stability issues. A number of polypeptides of WO03106654 are of relevance to the present invention. WO 2017/103159 also discloses a GH30 subfamily 8 polypeptide having xylanase activity, wherein the GH30 subfamily 8 polypeptide have xylanase activity of relevance to the present invention.

Corn is used around the world in animal feed and thus there is a need to render xylanses suitable for application in corn feeds activity and capable of breaking down the highly branched xylan backbone in the cell wall in order to release more xylose and other nutrients which are trapped inside the cell wall.

SUMMARY OF THE INVENTION

The invention provides for a composition, such as an animal feed composition, comprising polypeptide having GH30 xylanase activity, said composition further comprising an additive selected from the group consisting of a calcium source such as calcium chloride and a source of carbonate such as $NaHCO_3$. The inventors have found that the use of at least one of these additives increases the activity of GH30 enzymes at various pH levels. Accordingly, a first aspect of the invention is directed to a composition comprising i. one or more polypeptides having xylanase activity; and
ii. one or more sources of calcium; and/or
iii. one or more sources of carbonate, wherein the polypeptide is a GH30 xylanase.

The invention provides for composition for use as an animal feed or animal feed additive.

The invention further provides for an animal feed or animal feed additive comprising the composition as defined by the invention.

An interesting aspect of the invention is directed to an animal feed comprising an animal feed additive, one or more protein sources and one or more energy sources characterised in the animal feed further comprising one or more polypeptides having xylanase activity and one or more sources of calcium; and/or one or more sources of carbonate, wherein the polypeptide having xylanase activity is a GH30 family xylanase.

The invention is further directed to a method of improving the release of xylan from feedstuff comprising the use of a composition as defined by the invention.

SEQUENCE LISTING

SEQ ID NO 1 is the "wild-type" xylanase (as defined in WO03106654 by SEQ ID NO:190).

SEQ ID NO 2 comprises the sequence:

```
AANDVTVNIS AEKQVIRGFG GMNHPAWVGD LTAAQRETAF
GNGQNQLGFS ILRIHVDENR NNWYKEVETA KSAIKHGAIV
FASPWNPPSN MVETFNHNGD TSAKRLRYDK YAAYAQHLND
FVTFMKSNGV NLYAISIQNE PDYAHEWTWW TPQEILRFMR
ENAGSINARV IAPESFQYLK NLSDPILNDP QALANMDILG
THLYGTQVSQ FPYPLFKQKG AGKDLWMTEV YYPNSDNNSA
DRWPEALDVS QHIHNSMVEG DFQAYVWWYI RRSYGPMKED
GTISKRGYNM AHFSKFVRPG YVRIDATKNP NPNVYVSAYK
GDNKVVIVAI NKSNTGVNQN FVLQNGSASQ VSRWITSSNS
NLQPGTNLKV TDNHFWAHLP AQSVTTFVVI R
```

SEQ ID NO 3 comprises the sequence:

```
AASDATVRLS AEKQVIRGFG GMNHPAWIGD LTAAQRETAF
GNGQNQLGFS ILRIHVDENR NNWYREVETA KSAIKHGAIV
FASPWNPPSD MVETFNRNGD TSAKRLRYDK YAAYAKHLND
FVTFMKNNGV NLYAISVQNE PDYAHDWTWW TPQEILRFMK
ENAGSINARV IAPESFQYLK NISDPIVNDP KALANMDILG
AHLYGTQLNN FAYPLFKQKG AGKDLWMTEV YYPNSDNHSA
DRWPEALDVS HHIHNSMVEG DFQAYVWWYI RRSYGPMKED
GTISKRGYNM AHFSKFVRPG YVRVDATKSP ASNVYVSAYK
GDNKVVIVAI NKNNSGVNQN FVLQNGSVSQ VSRWITSSSS
NLQPGTNLNV TDNHFWAHLP AQSVTTFVAN LR
```

SEQ ID NO 4 comprises the sequence:

```
ANTDYWQNWTDG GGTVNAVNGS GGNYSVNWSN TGNFVVGKGW
TTGSPFRTIN YNAGVWAPNG NAYLTLYGWT RSPLIEYYVV
DSWGTYRPTG TYKGTVYSDG GTYDVYTTTR YDAPSIDGDK
TTFTQYWSVR QSKRPTGSNA TITFSNHVNA WKRYGMNLGS
NWSYQVLATE GYRSSGSSNV TVW
```

SEQ ID NO 5 comprises the sequence:

```
ASTDYWQNWTDG GGIVNAVNGS GGNYSVNWSN TGNFVVGKGW
TTGSPFRTIN YNAGVWAPNG NGYLTLYGWT RSPLIEYYVV
DSWGTYRPTG TYKGTVKSDG GTYDIYTTTR YNAPSIDGDR
TTFTQYWSVR QSKRPTGSNA TITFSNHVNA WKSHGMNLGS
NWAYQVMATE GYQSSGSSNV TVW
```

SEQ ID NO: 6 is the amino acid sequence of the mature GH30_8 xylanase from *Clostridium acetobutylicum*:
SEQ ID NO: 7 is the amino acid sequence of the mature GH30_8 xylanase from *Pseudoalteromonas tetraodonis*:
SEQ ID NO: 8 is the amino acid sequence of the mature GH30_8 xylanase from *Paenibacillus sp-19179*:
SEQ ID NO: 9 is the amino acid sequence of the mature GH30_8 xylanase *Pectobacterium carotovorum* subsp. *Carotovorum*:
SEQ ID NO: 10 is the amino acid sequence of the mature GH30_8 xylanase *Ruminococcus* sp. CAG:330
SEQ ID NO: 11 is the amino acid sequence of the mature GH30_8 xylanase *Streptomyces* sp-62627:
Arg
Leu Pro Ala Gln Ser Val Thr Thr Leu Val Thr Gly
SEQ ID NO: 12 is the amino acid sequence of the mature GH30_8 xylanase *Clostridium saccharobutylicum*:
SEQ ID NO: 13 is the amino acid sequence of the mature GH30_8 xylanase *Paenibacillus panacisoli*.
SEQ ID NO: 14 is the amino acid sequence of the mature GH30_8 xylanase Human Stool metagenome
SEQ ID NO: 15 is the amino acid sequence of the mature GH30_8 xylanase *Vibrio rhizosphaerae*:
SEQ ID NO: 16 is the amino acid sequence of a mature GH30 xylanase from *Bacillus subtilis*.
SEQ ID NO: 17 is the amino acid sequence of a mature GH30 xylanase from *Bacillus amyloliquefaciens*.
SEQ ID NO: 18 is the amino acid sequence of a mature GH30 xylanase from *Bacillus licheniformis*.
SEQ ID NO: 19 is the amino acid sequence of a mature GH30 xylanase from *Bacillus subtilis*.
SEQ ID NO:20 is the amino acid sequence of a mature GH30 xylanase from *Paenibacillus pabuli*.
SEQ ID NO: 21 is the amino acid sequence of a mature GH30 xylanase from *Bacillus amyloliquefaciens* HB-26.

BRIEF DESCRIPTION OF DRAWINGS

FIG. 1 of Example 1 shows that for each of the GH30 xylanases tested, an increase in the release xylan was observed. The increase in the release of xylan was not, however, observed when other xylanases were used, including commercially available GH11 xylanases. Reference means xylanase without added calcium source or carbonate source; Xylanase A is SEQ ID NO 1; Xylanase B is SEQ ID NO 2; Xylanase C is SEQ ID NO 3; Xylanase D is a GH11 xylanase; Xylanase E is a GH11 xylanase; Xylanase F is Belfeed B1100; Xylanase G is Econase XT.

DETAILED DESCRIPTION OF THE INVENTION

The invention is based on some key observations. Firstly, that the presence of either a calcium source or a carbonate source with various xylanases significantly improves the release of xylan oligomers from maize and other feeds compared to the same xylanases without the calcium or carbonate source. Secondly, this observation was only observed for GH30 xylanases. Experiments with GH11 xylanases and other commercial xylanases did not yield the observed improvement. Accordingly, a first aspect of the invention is directed to composition comprising
   i. one or more polypeptides having xylanase activity; and
   ii. one or more sources of calcium; and/or
   iii. one or more sources of carbonate.
wherein the polypeptide is a GH30 xylanase.

The term "xylanase" means a glucuronoarabinoxylan endo-1,4-beta-xylanase (E.C. 3.2.1.136) that catalyses the endohydrolysis of 1,4-beta-D-xylosyl links in some glucuronoarabinoxylans. Xylanase activity can be determined with 0.2% AZCL-glucuronoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-glucuronoxylan as substrate in 200 mM sodium phosphate pH 6. Endo-1,4-β-xylanases with characterized specificity EC 3.2.1.8, are to date classified under eight GH-families: GH5, GH8, GH10, GH11, GH30, GH43, GH51 and GH98.

The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The term "animal" refers to all animals except humans. Examples of animals are non-ruminants, and ruminants. Ruminant animals include, for example, animals such as sheep, goats, cattle, e.g., beef cattle, cows, and young calves, deer, yank, camel, llama and kangaroo. Non-ruminant animals include mono-gastric animals, e.g., pigs or swine (including, but not limited to, piglets, growing pigs, and sows); poultry such as turkeys, ducks and chicken (including but not limited to broiler chicks, layers); horses (including but not limited to hotbloods, coldbloods and warm bloods), young calves; fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish); and crustaceans (including but not limited to shrimps and prawns).

The term "animal feed" refers to any compound, preparation, or mixture suitable for, or intended for intake by an animal. Animal feed for a mono-gastric animal typically comprises concentrates as well as vitamins, minerals, enzymes, direct fed microbial, amino acids and/or other feed ingredients (such as in a premix) whereas animal feed for ruminants generally comprises forage (including roughage and silage) and may further comprise concentrates as well as vitamins, minerals, enzymes direct fed microbial, amino acid and/or other feed ingredients (such as in a premix).

The term "Arabinoxylan-containing material" means any material containing arabinoxylan. Arabinoxylan is a hemi-cellulose found in both the primary and secondary cell walls of plants, including woods and cereal grains, consisting of copolymers of two pentose sugars, arabinose and xylose. The arabinoxylan chain contains a large number of 1,4-linked xylose units. Many xylose units are substituted with 2-, 3- or 2,3-substituted arabinose residues.

Examples of arabinoxylan-containing material are forage, roughage, seeds and grains (either whole or prepared by crushing, milling, etc from, e.g., corn, oats, rye, barley, wheat), trees or hard woods (such as poplar, willow, eucalyptus, palm, maple, birch), bamboo, herbaceous and/or woody energy crops, agricultural food and feed crops, animal feed products, cassava peels, cocoa pods, sugar cane, sugar beet, locust bean pulp, vegetable or fruit pomaces, wood waste, bark, shavings, sawdust, wood pulp, pulping liquor, waste paper, cardboard, construction and demolition wood waste, industrial or municipal waste water solids or sludge, manure, byproduct from brewing and/or fermentation processes, wet distillers grain, dried distillers grain, spent grain, vinasse and bagasse.

Forage as defined herein also includes roughage. Forage is fresh plant material such as hay and silage from forage plants, grass and other forage plants, grass and other forage plants, seaweed, sprouted grains and legumes, or any combination thereof. Examples of forage plants are Alfalfa (Lucerne), birdsfoot trefoil, brassica (e.g., kale, rapeseed (canola), rutabaga (swede), turnip), clover (e.g., alsike clover, red clover, subterranean clover, white clover), grass (e.g., Bermuda grass, brome, false oat grass, fescue, heath grass, meadow grasses, miscanthus, orchard grass, ryegrass, switchgrass, Timothy-grass), corn (maize), hemp, millet, barley, oats, rye, sorghum, soybeans and wheat and vegetables such as beets. Crops suitable for ensilage are the ordinary grasses, clovers, alfalfa, vetches, oats, rye and maize. Forage further includes crop residues from grain production (such as corn stover; straw from wheat, barley, oat, rye and other grains); residues from vegetables like beet tops; residues from oilseed production like stems and leaves form soy beans, rapeseed and other legumes; and fractions from the refining of grains for animal or human consumption or from fuel production or other industries.

Roughage is generally dry plant material with high levels of fiber, such as fiber, bran, husks from seeds and grains and crop residues (such as stover, copra, straw, chaff, sugar beet waste).

Preferred sources of arabinoxylan-containing materials are forage, roughage, seeds and grains, sugar cane, sugar beet and wood pulp.

The term "body weight gain" means an increase in live weight of an animal during a given period of time, e.g., the increase in weight from day 1 to day 21.

The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

The term "expression" includes any step involved in the production of a variant including, but not limited to, transcription, post-transcriptional modification, translation, post-translational modification, and secretion.

The term "expression vector" means a linear or circular DNA molecule that comprises a polynucleotide encoding a variant and is operably linked to control sequences that provide for its expression.

The term "feed conversion ratio" the amount of feed fed to an animal to increase the weight of the animal by a specified amount. An improved feed conversion ratio means a lower feed conversion ratio. By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition.

The term "feed efficiency" means the amount of weight gain per unit of feed when the animal is fed ad-libitum or a specified amount of food during a period of time. By "increased feed efficiency" it is meant that the use of a feed additive composition according the present invention in feed results in an increased weight gain per unit of feed intake compared with an animal fed without said feed additive composition being present.

The term "fragment" means a polypeptide having one or more (e.g., several) amino acids absent from the amino and/or carboxyl terminus of a mature polypeptide; wherein the fragment has xylanase activity. In one aspect, a fragment comprises at least 330 amino acid residues, at least 350 amino acid residues.

In one aspect, a fragment comprises at least 330 amino acid residues of SEQ ID NO: 1, at least 350 amino acid residues of SEQ ID NO: 1, or at least 370 amino acid residues of SEQ ID NO: 1. In one aspect, a fragment comprises at least 330 amino acid residues of SEQ ID NO: 2, at least 350 amino acid residues of SEQ ID NO: 2, or at least 370 amino acid residues of SEQ ID NO: 2. In one aspect, a fragment comprises at least 330 amino acid residues of SEQ ID NO: 3, at least 350 amino acid residues of SEQ ID NO: 3, or at least 370 amino acid residues of SEQ ID NO: 3.

The term "highly branched xylan" means that more than 50% of xylosyl units in the arabinoxylan backbone are substituted. This is preferably calculated from linkage analysis as performed in Huismann et al. Carbohydrate Polymers, 2000, 42:269-279.

The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

The term "improved property" means a characteristic associated with a variant that is improved compared to the parent. Such improved properties include, but are not limited to, catalytic efficiency, catalytic rate, chemical stability, oxidation stability, pH activity, pH stability, specific activity, stability under storage conditions, substrate binding, substrate cleavage, substrate specificity, substrate stability, surface properties, thermal activity, and thermostability. In an embodiment, the improved property is improved thermostability.

The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

The term "mature polypeptide" means a polypeptide in its final form following translation and any post-translational modifications, such as N-terminal processing, C-terminal truncation, glycosylation, phosphorylation, etc.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

The term "mature polypeptide coding sequence" means a polynucleotide that encodes a mature polypeptide having xylanase activity.

The term "mutant" means a polynucleotide encoding a variant.

The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

The term "nutrient digestibility" means the fraction of a nutrient that disappears from the gastro-intestinal tract or a specified segment of the gastro-intestinal tract, e.g., the small intestine. Nutrient digestibility may be measured as the difference between what is administered to the subject and what. comes out in the faeces of the subject, or between what is administered to the subject and what remains in the digesta on a specified segment of the gastro intestinal tract, e.g., the ileum.

Nutrient digestibility as used herein may be measured by the difference between the intake of a nutrient and the excreted nutrient by means of the total collection of excreta during a period of time; or with the use of an inert marker that is not absorbed by the animal, and allows the researcher calculating the amount of nutrient that disappeared in the entire gastro-intestinal tract or a segment of the gastro-intestinal tract. Such an inert marker may be titanium dioxide, chromic oxide or acid insoluble ash. Digestibility may be expressed as a percentage of the nutrient in the feed, or as mass units of digestible nutrient per mass units of nutrient in the feed. Nutrient digestibility as used herein encompasses starch digestibility, fat digestibility, protein digestibility, and amino acid digestibility.

Energy digestibility as used herein means the gross energy of the feed consumed minus the gross energy of the faeces or the gross energy of the feed consumed minus the gross energy of the remaining digesta on a specified segment of the gastro-intestinal tract of the animal, e.g., the ileum. Metabolizable energy as used herein refers to apparent metabolizable energy and means the gross energy of the feed consumed minus the gross energy contained in the faeces, urine, and gaseous products of digestion. Energy digestibility and metabolizable energy may be measured as the difference between the intake of gross energy and the gross energy excreted in the faeces or the digesta present in specified segment of the gastro-intestinal tract using the same methods to measure the digestibility of nutrients, with appropriate corrections for nitrogen excretion to calculate metabolizable energy of feed.

The term "operably linked" means a configuration in which a control sequence is placed at an appropriate position relative to the coding sequence of a polynucleotide such that the control sequence directs expression of the coding sequence.

The term "parent" or "parent xylanase" means a xylanase to which a substitution is made to produce the xylanase variants of the present invention. The parent may be a naturally occurring (wild-type) polypeptide or a variant or fragment thereof.

The term "percentage solubilized xylan" means the amount of xylose measured in the supernatant after incubation with an enzyme compared to the total amount of xylose present in the substrate before the incubation with the enzyme. For the purpose of the present invention, the percentage solubilized xylan may be calculated using defatted destarched maize (DFDSM) as substrate. DFDSM is prepared according to 'Preparation of Defatted Destarched Maize (DFDSM)' in the experimental section.

The percentage solubilized xylan from defatted destarched maize (DFDSM) may be determined using the reaction conditions 20 μg enzyme/g DFDSM and incubation at 40° C., pH 5 for 2.5 hours as described in the 'Xylose solubilization assay' herein. Thus the term 'is performed under the reaction conditions 20 μg xylanase variant per gram defatted destarched maize (DFDSM) and incubation at 40° C., pH 5 for 2.5 hours' is to be understood that the percentage solubilised xylan is calculated as described in the 'Xylose solubilization assay' herein.

In a more detailed embodiment, 2% (w/w) DFDSM suspension was prepared in 100 mM sodium acetate, 5 mM CaCl$_2$, pH 5 and allowed to hydrate for 30 min at room temperature under gently stirring. After hydration, 200 μl substrate suspension was pipetted into a 96 well plate and mixed with 20 μl enzyme solution to obtain a final enzyme concentration of 20 PPM relative to substrate (20 μg enzyme/g substrate). The enzyme/substrate mixtures were left for hydrolysis in 2.5 h at 40° C. under gently agitation (500 RPM) in a plate incubator. After enzymatic hydrolysis, the enzyme/substrate plates were centrifuged for 10 min at 3000 RPM and 50 μl supernatant was mixed with 100 μl 1.6 M HCl and transferred to 300 μl PCR tubes and left for acid hydrolysis for 40 min at 90° C. in a PCR machine. Samples were neutralized with 125 μl 1.4 M NaOH after acid hydrolysis and loaded on the HPAE-PAD for mono-saccharide analysis.

The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), e.g., version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), e.g., version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

The term "subsequence" means a polynucleotide having one or more (e.g., several) nucleotides absent from the 5' and/or 3' end of a mature polypeptide coding sequence; wherein the subsequence encodes a fragment having xylanase activity.

The term "variant" means a polypeptide having xylanase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or at least 100% of the xylanase activity of the polypeptide of SEQ ID NO: 1.

The term "wild-type" xylanase means a xylanase expressed by a naturally occurring microorganism, such as a bacterium, yeast, or filamentous fungus found in nature.

SEQ ID NO 1 is a "wild-type" xylanase and is defined in WO03106654 by SEQ ID NO:190. Nine single site amino acid mutants (D8F, Q1IH, N12L, G17I, G60H, P64V, S65V, G68A & S79P) that have improved thermal tolerance relative to the wild type enzyme (as measured following a heat challenge at 80° C. for 20 minutes). Each of these variants are also suitable xylanases of the present invention. A "9X" variant was generated by combining all 9 single-site mutants into one enzyme. This mutant and smaller combinations of the mutants are also suitable xylanases of the present invention.

An embodiment of the invention relates to a composition, comprising one or more polypeptides having xylanase activity; and one or more sources of calcium; wherein the polypeptide is a GH30 xylanase. A further embodiment relates to a composition comprising one or more polypeptides having xylanase activity; and one or more sources of carbonate, wherein the polypeptide is a GH30 xylanase.

The source of calcium may be selected from the group consisting of calcium chloride, calcium phosphate, tricalcium citrate, calcium lactate, calcium lactate gluconate calcium carbonate, calcium citrate, calcium malate, calcium glubionate, calcium gluceptate, calcium gluconate and calcium acetate. Natural or synthetic sources of the calcium source is envisaged including food or feedstuff comprising said calcium sources. Calcium sources derived from natural sources such as leavy plants, vegetables, coral, dolomite and oystershell are suitable embodiments. In a suitable embodiment, the calcium source is calcium chloride.

The source of carbonate may be selected from the group consisting of $NaHCO_3$, $Na_2CO_3$, $LiHCO_3$, $KHCO_3$, $CaCO_3$, $Ca(HCO_3)_2$, $BaCO_3$, $FeCO_3$, $ZnCO_3$, $NH_4HCO_3$ and $(NH_4)_2 CO_3$.

Natural or synthetic sources of the carbonate source is envisaged including and food or feedstuff comprising said carbonate sources. In a suitable embodiment, the carbonate source is selected from $NaHCO_3$, $LiHCO_3$, $KHCO_3$, such as $NaHCO_3$.

In an embodiment of the invention, the one or more polypeptides having xylanase activity are selected from the group consisting of a) a polypeptide having at least 80% sequence identity, such as at least 90% sequence identity, such as at least 95% sequence identity, such as at least 98% sequence identity, such as least 99% sequence identity to the polypeptide of SEQ ID NO 1.

b) a polypeptide having at least 80% sequence identity, such as at least 90% sequence identity, such as at least 95% sequence identity, such as at least 98% sequence identity, such as least 99% sequence identity to the polypeptide of SEQ ID NO 2.

c) a polypeptide having at least 80% sequence identity, such as at least 90% sequence identity, such as at least 95% sequence identity, such as at least 98% sequence identity, such as least 99% sequence identity to the polypeptide of SEQ ID NO 3.

d) a polypeptide having at least 80% sequence identity, such as at least 90% sequence identity, such as at least 95% sequence identity, such as at least 98% sequence identity, such as least 99% sequence identity to the polypeptide of SEQ ID NO 6.

e) a polypeptide having at least 80% sequence identity, such as at least 90% sequence identity, such as at least 95% sequence identity, such as at least 98% sequence identity, such as least 99% sequence identity to the polypeptide of SEQ ID NO: 7;

f) a polypeptide having at least 80% sequence identity, such as at least 90% sequence identity, such as at least 95% sequence identity, such as at least 98% sequence identity, such as least 99% sequence identity to the polypeptide of SEQ ID NO: 8;

g) a polypeptide having at least 92% sequence identity, such as at least 90% sequence identity, such as at least 95% sequence identity, such as at least 98% sequence identity, such as least 99% sequence identity to the polypeptide of SEQ ID NO: 11;

h) a polypeptide having at least 80% sequence identity, such as at least 90% sequence identity, such as at least 95% sequence identity, such as at least 98% sequence identity, such as least 99% sequence identity to the polypeptide of SEQ ID NO: 12;

i) a polypeptide having at least 80% sequence identity, such as at least 90% sequence identity, such as at least 95% sequence identity, such as at least 98% sequence identity, such as least 99% sequence identity to the polypeptide of SEQ ID NO: 13;

j) a polypeptide having at least 80% sequence identity, such as at least 90% sequence identity, such as at least 95% sequence identity, such as at least 98% sequence identity, such as least 99% sequence identity to the polypeptide of SEQ ID NO: 14;

k) a polypeptide having at least 80% sequence identity, such as at least 90% sequence identity, such as at least 95% sequence identity, such as at least 98% sequence identity, such as least 99% sequence identity to the polypeptide of SEQ ID NO: 15;

l) a polypeptide having at least 80% sequence identity, such as at least 90% sequence identity, such as at least 95% sequence identity, such as at least 98% sequence identity, such as least 99% sequence identity to the polypeptide of SEQ ID NO: 16;

m) a polypeptide having at least 80% sequence identity, such as at least 90% sequence identity, such as at least 95% sequence identity, such as at least 98% sequence identity, such as least 99% sequence identity to the polypeptide of SEQ ID NO: 17 n) a polypeptide having at least 80% sequence identity, such as at least 90% sequence identity, such as at least 95% sequence identity, such as at least 98% sequence identity, such as least 99% sequence identity to the polypeptide of SEQ ID NO: 18;

o) a polypeptide having at least 80% sequence identity, such as at least 90% sequence identity, such as at least 95% sequence identity, such as at least 98% sequence identity, such as least 99% sequence identity to the polypeptide of SEQ ID NO: 19, p) a polypeptide having at least 80% sequence identity, such as at least 90% sequence identity, such as at least 95% sequence identity, such as at least 98% sequence identity, such as least 99% sequence identity to the polypeptide of SEQ ID NO: 20;

q) a polypeptide having at least 80% sequence identity, such as at least 90% sequence identity, such as at least 95% sequence identity, such as at least 98% sequence identity, such as least 99% sequence identity to the polypeptide of SEQ ID NO: 21;

r) a variant of the polypeptide of SEQ ID NO: 1, SEQ ID NO: 2, SEQ ID NO: 3, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21 comprising one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

s) a variant of the polypeptide of SEQ ID NO: 1 comprising one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39 positions;

t) a polypeptide comprising the polypeptide of (a), (b), (c), (d), (e), (f), (g), (h), (i), (j), (k) or (l) and a N-terminal and/or C-terminal His-tag and/or HQ-tag; and u) a fragment of a polypeptide of (a), (b), (c), (d), (e), (f), (g), (h), (i), (j), (k), (l) or (m) having at least 90% of the length of the mature polypeptide.

The one or more polypeptides may be, for instance, a mature GH30 xylanase from *Bacillus subtilis*, a mature GH30 xylanase from *Bacillus amyloliquefaciens*, a mature GH30 xylanase from *Bacillus licheniformis*, a mature GH30 xylanase from *Paenibacillus pabuli*, a mature GH30 xylanase from *Bacillus amyloliquefaciens*.

The one or more polypeptides having xylanase activity are selected from the group consisting of a polypeptide having at least 80% sequence identity to the polypeptide of SEQ ID NO 1, SEQ ID NO 2, SEQ ID NO 3, SEQ ID NO 16, SEQ ID NO 17, SEQ ID NO 18, SEQ ID NO 19, SEQ ID NO 20 and SEQ ID NO 21. According to the invention, the one or more polypeptides having xylanase activity may be selected from the group consisting of a polypeptide having at least 85% sequence identity, such as at least 90% identity, such as at least 95% identity, such as at least 98% identity, such as at least 99% identity to the polypeptide of SEQ ID NO 1, SEQ ID NO 2, SEQ ID NO 3, SEQ ID NO 16, SEQ ID NO 17, SEQ ID NO 18, SEQ ID NO 19, SEQ ID NO 20 and SEQ ID NO 21.

The composition of the invention is typically such that the source of calcium; and/or a source of carbonate is present in an amount such that the solubilisation of arabinoxylan oligomers is increased, as compared to an identical composition devoid of a source of calcium and/or a source of carbonate, as measured by the release of xylan oligomers as evaluated by measuring the fluorescence of the supernatant with excitation at 320 nm and emission at 440 nm with activity of the enzyme measured in arabinoxylan hydrolysing unit (AHU).

Otherwise stated, the composition of the invention is typically such that it is characterized in that it increases the solubilisation of arabinoxylan oligomers, as compared to an identical composition devoid of a source of calcium and/or a source of carbonate, as measured by the release of xylan oligomers as evaluated by measuring the fluorescence of the supernatant with excitation at 320 nm and emission at 440 nm with activity of the enzyme measured in arabinoxylan hydrolysing unit (AHU).

The composition of the invention is intended for use in the improvement of the solubilisation of arabinoxylan oligomers, as compared to an identical composition devoid of a source of calcium and/or a source of carbonate. Thus is suitably by the release of xylan oligomers as evaluated by measuring the fluorescence of the supernatant with excitation at 320 nm and emission at 440 nm with activity of the enzyme measured in arabinoxylan hydrolysing unit (AHU).

The composition of the invention is for use as an animal feed or animal feed additive. Accordingly, a further aspect of the invention is directed to an animal feed or animal feed additive comprising the composition of the invention. A related aspect of the invention is directed to an animal feed comprising an animal feed additive, one or more protein sources and one or more energy sources characterised in the animal feed further comprises one or more polypeptides having xylanase activity and one or more sources of calcium; and/or one or more sources of carbonate, wherein the polypeptide having xylanase activity is a GH30 family xylanase.

A further aspect of the invention relates to an animal feed additive, or an animal feed comprising one or more polypeptides having xylanase activity; and one or more sources of calcium and/or one or more sources of carbonate; wherein the polypeptide is a GH30 xylanase. Similarly, an aspect of the invention is directed to preparing an animal feed additive or an animal feed or feedstuff comprising one or more polypeptides having xylanase activity; and one or more sources of calcium and/or one or more sources of carbonate; wherein the polypeptide is a GH30 xylanase.

A further aspect of the invention is directed to a method of improving the release of xylan from feedstuff comprising the use of a composition of the invention, an animal feed of the invention, or an animal feed additive of the invention.

An aspect of the invention is directed to a method of solubilising xylan from plant based material, comprising treating plant based material with a combination of
  i. one or more polypeptides having xylanase activity; and
  ii. one or more sources of calcium; and/or
  iii. one or more sources of carbonate; wherein the polypeptide is a GH30 xylanase.

Suitably the plant based material is from the sub-family Panicoideae including maize, corn, sorghum, switchgrass, millet, pearl millet, foxtail millet or in a processed form such as milled corn, milled maize, defatted maize, defatted destarched maize, milled sorghum, milled switchgrass, milled millet, milled foxtail millet, milled pearl millet, or any combination thereof.

Further aspects of the invention relate to a method of preparing an animal feed comprising the composition of the invention or the animal feed additive of the invention with plant based material. Similarly, the invention is directed to a method for improving the nutritional value of an animal feed comprising plant based material, comprising adding to the feed the composition the invention or a combination of
  i. one or more polypeptides having xylanase activity; and
  ii. one or more sources of calcium; and/or
  iii. one or more sources of carbonate; wherein the polypeptide is a GH30 xylanase.

The composition of the invention may be those conventionally used in feed compositions for feed additives. The composition may comprise further enzymatic components, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, and/or alternate xylanase.

The compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

The dosage of the polypeptide composition of the invention and other conditions under which the composition is used may be determined on the basis of methods known in the art.

The compositions may further comprise one or more probiotics. In an embodiment, the probiotic is selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococsus acidilactici, Pediococcus* sp., *Propionibacterium thoenii, Propionibacterium* sp. and *Streptococcus* sp. or any combination thereof.

In an embodiment, the composition comprises one or more formulating agents as disclosed herein, preferably one or more of the compounds selected from the list consisting of glycerol, ethylene glycol, 1,2-propylene glycol or 1,3- propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose.

In an embodiment, the composition comprises one or more components selected from the list consisting of vitamins, minerals and amino acids.

Formulation

The enzyme of the invention may be formulated as a liquid or a solid. For a liquid formulation, the formulating agent may comprise a polyol (such as e.g. glycerol, ethylene glycol or propylene glycol), a further salt (such as e.g. sodium chloride, sodium benzoate, potassium sorbate) or a sugar or sugar derivative (such as e.g. dextrin, glucose, sucrose, and sorbitol). Thus in one embodiment, the composition is a liquid composition comprising the composition comprising i. one or more polypeptides having xylanase activity; and ii. one or more sources of calcium; and/or iii. one or more sources of carbonate, wherein the polypeptide is a GH30 xylanase and one or more formulating agents selected from the list consisting of glycerol, ethylene glycol, 1,2-propylene glycol, 1,3-propylene glycol, sodium chloride, sodium benzoate, potassium sorbate, dextrin, glucose, sucrose, and sorbitol. The liquid formulation may be sprayed onto the feed after it has been pelleted or may be added to drinking water given to the animals.

For a solid formulation, the formulation may be for example as a granule, spray dried powder or agglomerate (e.g. as disclosed in WO2000/70034). The formulating agent may comprise a salt (organic or inorganic zinc, sodium, potassium or calcium salts such as e.g. such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol).

In one embodiment, the composition is a solid composition, such as a spray dried composition, comprising i. one or more polypeptides having xylanase activity; and ii. one or more sources of calcium; and/or iii. one or more sources of carbonate, wherein the polypeptide is a GH30 xylanase and one or more formulating agents selected from the list consisting of sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose. In a preferred embodiment, the formulating agent is selected from one or more of the following compounds: sodium sulfate, dextrin, cellulose, sodium thiosulfate, magnesium sulfate and calcium carbonate.

The present invention also relates to enzyme granules/particles comprising the composition of the invention optionally combined with one or more additional enzymes. The granule is composed of a core, and optionally one or more coatings (outer layers) surrounding the core.

Typically the granule/particle size, measured as equivalent spherical diameter (volume based average particle size), of the granule is 20-2000 μm, particularly 50-1500 μm, 100-1500 μm or 250-1200 μm.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier. Preparation methods include known feed and granule formulation technologies, e.g.:

a) spray dried products, wherein a liquid enzyme-containing solution is atomized in a spray drying tower to form small droplets which during their way down the drying tower dry to form an enzyme-containing particulate material;

b) layered products, wherein the enzyme is coated as a layer around a pre-formed inert core particle, wherein an enzyme-containing solution is atomized, typically in a fluid bed apparatus wherein the pre-formed core particles are fluidized, and the enzyme-containing solution adheres to the core particles and dries up to leave a layer of dry enzyme on the surface of the core particle. Particles of a desired size can be obtained this way if a useful core particle of the desired size can be found. This type of product is described in, e.g., WO 97/23606;

c) absorbed core particles, wherein rather than coating the enzyme as a layer around the core, the enzyme is absorbed onto and/or into the surface of the core. Such a process is described in WO 97/39116.

d) extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme;

e) prilled products, wherein an enzyme-containing powder is suspended in molten wax and the suspension is sprayed, e.g., through a rotating disk atomiser, into a cooling chamber where the droplets quickly solidify (Michael S. Showell (editor); *Powdered detergents*; Surfactant Science Series; 1998; vol. 71; page 140-142; Marcel Dekker). The product obtained is one wherein the enzyme is uniformly distributed throughout an inert material instead of being concentrated on its surface. Also U.S. Pat. Nos. 4,016,040 and 4,713,245 are documents relating to this technique;

f) mixer granulation products, wherein a liquid is added to a dry powder composition of, e.g., conventional granulating components, the enzyme being introduced either via the liquid or the powder or both. The liquid and the powder are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 and related documents EP 170360, EP 304332, EP 304331, WO 90/09440 and WO 90/09428. In a particular product of this process wherein various high-shear mixers can be used as granulators, granulates consisting of enzyme as enzyme, fillers and binders etc. are mixed with cellulose fibres to reinforce the particles to give the so-called T-granulate. Reinforced particles, being more robust, release less enzymatic dust.

g) size reduction, wherein the cores are produced by milling or crushing of larger particles, pellets, tablets, briquettes etc. containing the enzyme. The wanted core particle fraction is obtained by sieving the milled or crushed product. Over and undersized particles can be recycled. Size reduction is described in (Martin Rhodes (editor); Principles of Powder Technology; 1990; Chapter 10; John Wiley & Sons);

h) fluid bed granulation, which involves suspending particulates in an air stream and spraying a liquid onto the fluidized particles via nozzles. Particles hit by spray droplets get wetted and become tacky. The tacky particles collide with other particles and adhere to them and form a granule;

i) the cores may be subjected to drying, such as in a fluid bed drier. Other known methods for drying granules in the feed or detergent industry can be used by the skilled person. The drying preferably takes place at a product temperature of from 25 to 90° C. For some enzymes it is important the cores comprising the enzyme contain a low amount of water before coating. If water sensitive enzymes are coated before excessive water is removed, it will be trapped within the core and it may affect the activity of the enzyme negatively. After drying, the cores preferably contain 0.1-10% w/w water.

The core may include additional materials such as fillers, fibre materials (cellulose or synthetic fibres), stabilizing agents, solubilizing agents, suspension agents, viscosity regulating agents, light spheres, plasticizers, salts, lubricants and fragrances.

The core may include a binder, such as synthetic polymer, wax, fat, or carbohydrate.

The core may include a salt of a multivalent cation, a reducing agent, an antioxidant, a peroxide decomposing catalyst and/or an acidic buffer component, typically as a homogenous blend.

In one embodiment, the core comprises a material selected from the group consisting of salts (such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol), sugar or sugar derivative (such as e.g. sucrose, dextrin, glucose, lactose, sorbitol), small organic molecules, starch, flour, cellulose and minerals and clay minerals (also known as hydrous aluminium phyllosilicates). In one embodiment, the core comprises a clay mineral such as kaolinite or kaolin.

The core may include an inert particle with the enzyme absorbed into it, or applied onto the surface, e.g., by fluid bed coating.

The core may have a diameter of 20-2000 μm, particularly 50-1500 μm, 100-1500 μm or 250-1200 μm.

The core may be surrounded by at least one coating, e.g., to improve the storage stability, to reduce dust formation during handling, or for coloring the granule. The optional coating(s) may include a salt and/or wax and/or flour coating, or other suitable coating materials.

The coating may be applied in an amount of at least 0.1% by weight of the core, e.g., at least 0.5%, 1% or 5%. The amount may be at most 100%, 70%, 50%, 40% or 30%.

The coating is preferably at least 0.1 μm thick, particularly at least 0.5 μm, at least 1 μm or at least 5 μm. In some embodiments the thickness of the coating is below 100 μm, such as below 60 μm, or below 40 μm.

The coating should encapsulate the core unit by forming a substantially continuous layer. A substantially continuous layer is to be understood as a coating having few or no holes, so that the core unit is encapsulated or enclosed with few or no uncoated areas. The layer or coating should in particular be homogeneous in thickness.

The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight of a salt, e.g., at least 65%, at least 70%, at least 75%, at least 80%, at least 85%, at least 90%, at least 95% or at least 99% by weight.

The salt may be added from a salt solution where the salt is completely dissolved or from a salt suspension wherein the fine particles are less than 50 μm, such as less than 10 μm or less than 5 μm.

The salt coating may comprise a single salt or a mixture of two or more salts. The salt may be water soluble, in particular having a solubility at least 0.1 g in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, sorbate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO1997/05245, WO1998/54980, WO1998/55599, WO2000/70034, WO2006/034710, WO2008/017661, WO2008/017659, WO2000/020569, WO2001/004279, WO1997/05245, WO2000/01793, WO2003/059086, WO2003/059087, WO2007/031483, WO2007/031485, WO2007/044968, WO2013/192043, WO2014/014647 and WO2015/197719 or polymer coating such as described in WO 2001/00042.

Specific examples of suitable salts are NaCl (CH20° C.=76%), Na2CO3 (CH20° C.=92%), NaNO3 (CH20° C.=73%), Na2HPO4 (CH20° C.=95%), Na3PO4 (CH25° C.=92%), NH4Cl (CH20° C.=79.5%), (NH4)2HPO4 (CH20° C.=93.0%), NH4H2PO4 (CH20° C.=93.1%), (NH4)2SO4 (CH20° C.=81.1%), KCl (CH20° C.=85%), K2HPO4 (CH20° C.=92%), KH2PO4 (CH20° C.=96.5%), KNO3 (CH20° C.=93.5%), Na2SO4 (CH20° C.=93%), K2SO4 (CH20° C.=98%), KHSO4 (CH20° C.=86%), MgSO4 (CH20° C.=90%), ZnSO4 (CH20° C.=90%) and sodium citrate (CH25° C.=86%). Other examples include NaH2PO4, (NH4)H2PO4, CuSO4, Mg(NO3)2, magnesium acetate, calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, sodium acetate, sodium benzoate, sodium citrate, sodium sulfate, zinc acetate, zinc benzoate, zinc carbonate, zinc chloride, zinc citrate and zinc sorbate.

The salt may be in anhydrous form, or it may be a hydrated salt, i.e. a crystalline salt hydrate with bound water(s) of crystallization, such as described in WO 99/32595. Specific examples include anhydrous sodium sulfate (Na2SO4), anhydrous magnesium sulfate (MgSO4), magnesium sulfate heptahydrate (MgSO4.7H2O), zinc sulfate heptahydrate (ZnSO4.7H2O), sodium phosphate dibasic heptahydrate (Na2HPO4.7H2O), magnesium nitrate hexahydrate (Mg(NO3)2(6H2O)), sodium citrate dihydrate and magnesium acetate tetrahydrate.

Preferably the salt is applied as a solution of the salt, e.g., using a fluid bed.

A wax coating may comprise at least 60% by weight of a wax, e.g., at least 65%, at least 70%, at least 75%, at least 80%, at least 85%, at least 90%, at least 95% or at least 99% by weight.

Specific examples of waxes are polyethylene glycols; polypropylenes; Carnauba wax; Candelilla wax; bees wax; hydrogenated plant oil or animal tallow such as polyethylene glycol (PEG), methyl hydroxy-propyl cellulose (MHPC), polyvinyl alcohol (PVA), hydrogenated ox tallow, hydrogenated palm oil, hydrogenated cotton seeds and/or hydrogenated soy bean oil; fatty acid alcohols; mono-glycerides and/or di-glycerides, such as glyceryl stearate, wherein stearate is a mixture of stearic and palmitic acid; microcrystalline wax; paraffin's; and fatty acids, such as hydrogenated linear long chained fatty acids and derivatives thereof. A preferred wax is palm oil or hydrogenated palm oil.

The granule may comprise a core comprising the composition of the invention, one or more salt coatings and one or more wax coatings. Examples of enzyme granules with multiple coatings are shown in WO1993/07263, WO1997/23606 and WO2016/149636.

Non-dusting granulates may be produced, e.g., as disclosed in U.S. Pat. Nos. 4,106,991 and 4,661,452 and may optionally be coated by methods known in the art. The coating materials can be waxy coating materials and film-forming coating materials. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and tri-glycerides of fatty acids. Examples of film-forming coating materials suitable for application by fluid bed techniques are given in GB 1483591.

The granulate may further comprise one or more additional enzymes. Each enzyme will then be present in more granules securing a more uniform distribution of the enzymes, and also reduces the physical segregation of different enzymes due to different particle sizes. Methods for producing multi-enzyme co-granulates is disclosed in the ip.com disclosure IPCOM000200739D.

Another example of formulation of enzymes by the use of co-granulates is disclosed in WO 2013/188331.

The present invention also relates to protected enzymes prepared according to the method disclosed in EP 238,216.

Thus, in a further aspect, the present invention provides a granule, which comprises:
(a) comprising i. one or more polypeptides having xylanase activity; and ii. one or more sources of calcium; and/or iii. one or more sources of carbonate, wherein the polypeptide is a GH30 xylanase, and
(b) a coating consisting of one or more layer(s) surrounding the core.

In one embodiment, the coating comprises a salt coating as described herein. In one embodiment, the coating comprises a wax coating as described herein. In one embodiment, the coating comprises a salt coating followed by a wax coating as described herein.

EXAMPLES

Example 1

Enzymatic Activity Assay

Introduction

The activity of the enzymes in hydrolyzing maize arabinoxylans was measured spectrophotometrically after enzymatic hydrolysis of an arabinoxylan-rich substrate such as defatted destarched (DFDS) maize. Briefly, a 4 w/v % slurry of DFDS (de-fatted de-starched) maize was incubated for 30 minutes at pH 2.90±0.1 and at 40° C. Then the solution pH was adjusted to 5.0 and enzymes were added to the slurry. After a 2 hours' incubation at 40° C., the fluorescence (Ex=320 nm, Em=440 nm) of the supernatant was measured.

DFDS Maize Slurry

Four different 4% w/v slurry of DFDS maize were prepared from DFDS maize milled to a 0.5 mm particle size mixed with (i) deionized water (dH$_2$O), (ii) deionized water and 10 mM CaCl$_2$, (iii) deionized water and 10 mM NaHCO$_3$, and (iv) 2% v/v sunflower oil. The four solutions (dH$_2$O, dH$_2$O and 10 mM CaCl$_2$, dH$_2$O and 10 mM NaHCO$_3$, dH$_2$O and sunflower oil) were heated in separate glass beakers to a temperature of approximately 40° C. while stirring. The DFDS maize was then added to the heated solutions. The slurries were stirred while being heated to 40° C. and the pH was adjusted to 2.9±0.1 with 4M HCl. The slurries were then transferred with pre-wetted wide-bore pipettes to the vessels of 24 deep well plate (DWP). The slurries were pipetted from an approximately central point in the mix and 2.5 mL slurry was transferred to each well. The DWP was transferred to an incubator and the slurries were mixed with 500 rpm and heated to 40° C. for 30 minutes. The pH of the slurries was adjusted to 5.0 by addition of 1 M NaOH.

Dilution of Enzymes

The enzymes were diluted to their desired concentrations (1 ppm) in deionized water. The enzymes dilution was based on the concentration of the enzyme in mg enzyme protein per mL (mg EP/mL) and the mass (kg) of dry matter (soybean meal) in each incubation vessel. Commercial products were diluted to a concentration of 50 mg/mL in dH$_2$O. Following 45 minutes mixing at room temperature, the enzymes were filtered by using a syringe fitted with a 1.2 μm filter. The filtered enzymes were further diluted so that the concentration in the final vessel corresponded to the recommended dosage of the commercial product.

Incubation of Xylanase with DFDS Maize

The incubation vessels with the 4 w/v % slurry of DFDS maize were heated to a stable temperature of 40±2° C. while stirring (500 rpm). Then the diluted enzymes were added to their respective incubation vessels in the volumes required to reach their desired concentrations (in mg EP/kg DFDS maize). Each enzyme treatment was incubated in sextuplicates. Additionally, six incubation vessels were included without enzymes as blank treatments to obtain the fluorescence baseline in the supernatant of the DFDS maize slurry. The incubation vessels were incubated at 40±2° C., while stirring for 2 hours. After incubation, the vessels were centrifuged at 4000 rpm at 5° C. for 15 minutes. 1 mL of supernatant was then transferred from each well to the wells of a 96 DWP.

Fluorescence Measurements

40 µL of the supernatant were transferred from the 96 DWP to a different 96 DWP(2). 280 µL deionized $H_2O$ was added to each sample in the 96 DWP(2) and the plate was mixed for 1 minute at 1000 rpm. 200 µL of the solution was then from 96 DWP(2) to a 96 microtiter plate (MTP) and the fluorescence of the samples was measured with excitation at 320 nm and emission at 440 nm by using a Tecan Infinite M200 spectrophotometer.

Arabinoxylan consists of a β-1,4 linked xylan backbone with the xylose monomers substituted with arabinofuranosyle residues further substituted with ferulic acid (1). Ferulic acid (4-hydroxy-3-methoxycinnamic) is an organic compound with fluorescence properties (2). As the xylanases hydrolyse the maize cell wall arabinoxylan, arabinoxylan oligomers containing ferulic acid are also solubilized. Therefore, the hydrolysing activity of the enzymes can be evaluated by measuring the fluorescence of the supernatant with excitation at 320 nm and emission at 440 nm. The activity of the enzyme is measured in arabinoxylan hydrolysing unit (AHU), where 1 AHU is defined as the increase in fluorescence (Ex. 320 nm/Em. 440 nm) of 1 A.U. from 100 mg of DFDSM. The obtained results were corrected for blanks without any addition of enzymes. Data were analysed by using the Tukey-Kramer HSD test (SAS JMP®, 2015, sas. jmp software) at the 0.05 level of significance.

Results: Performance of Enzymes in Presence of Calcium and Carbonate

The release of xylan oligomers from DFDS maize of three GH30 xylanases of the invention (SEQ ID NO: 1, 2, 3) and two known GH11 xylanases (SEQ ID No: 4, 5) and three commercial GH11 products (Belfeed B1100, Econase XT, and SafizymeXP 500) were determined using the Enzymatic Activity Assay and the results are presented in Table 1 below.

TABLE 1

Solubilization of arabinoxylan oligomers using xylanase

| Enzyme tested | AHU in $dH_2O$ | AHU with 10 mM $CaCl_2$ | AHU with 10 mM $NaHCO_3$ |
|---|---|---|---|
| SEQ ID NO 1 | $1273^B$ | $1559^A$ | $1602^A$ |
| SEQ ID NO 2 | $896^D$ | $1095^{B,C}$ | $1142^{B,C}$ |
| SEQ ID NO 3 | $974^{C,D}$ | $1224^B$ | $1217^B$ |
| SEQ ID NO 4 | $2.5^{E,F}$ | $13.1^{E,F}$ | $79.6^{E,F}$ |
| SEQ ID NO 5 | $-12.1^F$ | $-7.38^F$ | $37.6^{E,F}$ |
| Belfeed B1100 | $76.4^{E,F}$ | $93.5^{E,F}$ | $173^E$ |
| Econase XT | $95.6^{E,F}$ | $40.4^{E,F}$ | $138^{E,F}$ |
| SafizymeXP 500 | $88.5^{E,F}$ | $82.1^{E,F}$ | $75^{E,F}$ |

$^{A,B,C,D,E,F}$Means not sharing a common letter are significantly different (TUKEY-Kramer test, $p < 0.05$).

Example 2

Enzymatic Activity Assay after Gastric Challenge

Introduction

For measuring the activity of the enzymes after gastric challenge, the enzymes were incubated with a 4 w/v % slurry of DFDS (de-fatted de-starched) maize for 15 minutes at pH 2.90±0.1 and 40° C. Then the solution pH was adjusted to 5.0 with NaOH and the slurry was further incubated for 2 hours at 40° C. Following incubation, the fluorescence (Ex=320 nm, Em=440 nm) of the supernatant was then measured.

DFDS Maize Slurry

Four different 4% w/v slurry of DFDS maize were prepared from DFDS maize milled to a 0.5 mm particle size mixed with (i) deionized water (dH2O), (ii) deionized water and 10 mM $CaCl_2$, (iii) deionized water and 10 mM $NaHCO_3$, and (iv) 2% v/v sunflower oil. The four solutions were heated in separate glass beakers to a temperature of approximately 40° C. while stirring. The DFDS maize was then added to the heated solutions. The slurries were stirred while being heated to 40° C. and the pH was adjusted to 2.9±0.1 with 4M HCl. The slurries were then transferred with pre-wetted wide-bore pipettes to the vessels of 24 deep well plate (DWP). The slurries were pipetted from an approximately central point in the mix and 2.5 mL slurry was transferred to each well. The DWP was transferred to an incubator and the slurries were mixed with 500 rpm and heated to 40° C. for 30 minutes.

Dilution of Enzymes

The enzymes were diluted to their desired concentrations (1 ppm) in deionized water. The enzymes dilution was based on the concentration of the enzyme in mg enzyme protein per mL (mg EP/mL) and the mass (kg) of dry matter (soybean meal) in each incubation vessel. Commercial products were diluted to a concentration of 50 mg/mL in $dH_2O$. Following 45 minutes mixing at room temperature, the enzymes were filtered by using a syringe fitted with a 1.2 µm filter. The filtered enzymes were further diluted so that the concentration in the final vessel corresponded to the recommended dosage of the commercial product.

Incubation of Xylanase with DFDS Maize

The incubation vessels with the 4 w/v % slurry of DFDS maize were heated to a stable temperature of 40±2° C. while stirring (500 rpm). Then the diluted enzymes were added to their respective incubation vessels in the volumes required to reach their desired concentrations (in mg EP/kg DFDS maize). Each enzyme treatment was incubated in sextuplicates. Additionally, six incubation vessels were included without enzymes as blank treatments to obtain the fluorescence baseline in the supernatant of the DFDS maize slurry. The incubation vessels were incubated at 40±2° C. while stirring at 500 rpm for 15 minutes. The pH of the slurries was adjusted to 5.0 by addition of 1 M NaOH and the slurries were incubated for 2 hours at 40±2° C. After incubation, the vessels were centrifuged at 4000 rpm at 5° C. for 15 minutes. 1 mL of supernatant was then transferred from each well to the wells of a 96 DWP.

Fluorescence Measurements

40 µL of the supernatant were transferred from the 96 DWP to a different 96 DWP(2). 280 µL deionized $H_2O$ was added to each sample in the 96 DWP(2) and the plate was mixed for 1 minute at 1000 rpm. 200 µL of the solution was then from 96 DWP(2) to a 96 microtiter plate (MTP) and the fluorescence of the samples was measured with excitation at 320 nm and emission at 440 nm by using a Tecan Infinite M200 spectrophotometer.

Arabinoxylan consists of a β-1,4 linked xylan backbone with the xylose monomers substituted with arabinofuranosyle residues further substituted with ferulic acid (1). Ferulic acid (4-hydroxy-3-methoxycinnamic) is an organic compound with fluorescence properties (2). As the xylanases hydrolyse the maize cell wall arabinoxylan, arabinoxylan oligomers containing ferulic acid are also solubilized. Therefore, the hydrolysing activity of the enzymes can be evaluated by measuring the fluorescence of the supernatant with excitation at 320 nm and emission at 440 nm. The activity of the enzyme is measured in arabinoxylan hydrolysing unit (AHU), where 1 AHU is defined as the increase in fluorescence (Ex. 320 nm/Em. 440 nm) of 1 A.U. from 100 mg of DFDSM. The obtained results were corrected for blanks without any addition of enzymes. Data were analysed by using the Tukey-Kramer HSD test (SAS JMP®, 2015, sas. jmp software) at the 0.05 level of significance.

(1) Fluorescence detection and measurement of ferulic acid in wheat milling fractions by microscopy and HPLC. Veranush Pussayanawin, David L. Wetzel, and R. G. Fulcher. Journal of Agricultural and Food Chemistry 1988 36 (3), 515-520. DOI: 10.1021/jf00081a027

(2) UV-induced blue-green and far-red fluorescence along wheat leaves: a potential signature of leaf ageing. S. Meyer, A. Cartelat, I. Moya and Z. G. Cerovic. Journal of Experimental Botany, Vol. 54, No. 383, pp. 757-769, February 2003. DOI: 10.1093/jxb/erg063

Example 3: Performance of Enzyme Xylanase of SEQ ID NO 1 in Presence of Calcium, Carbonate and Oil The release of xylan oligomers from DFDS maize of the xylanase of the invention (SEQ ID NO: 1) was determined using the Enzymatic Activity Assay and the results are presented in Table 2 below.

TABLE 2

Solubilization of arabinoxylan oligomers using xylanase (SEQ. ID NO: A)

| Enzyme tested | AHU in dH$_2$O | AHU with 10 mM CaCl$_2$ | AHU with 10 mM NaHCO$_3$ | AHU with 2% v/v sunflower oil |
|---|---|---|---|---|
| SEQ ID NO 1 | 1273$^B$ | 1559$^A$ | 1602$^A$ | 1256$^B$ |

$^{A,B}$Means not sharing a common letter are significantly different (TUKEY-Kramer test, p < 0.05).

Example 4: Activity after Gastric Stability of Enzymes in Presence of Calcium and Carbonate The release of xylan oligomers from DFDS maize of three xylanases of the invention (SEQ ID NO: 1, 2, 3) and a known GH11 xylanases (SEQ ID No: 4) after gastric challenge were determined using the Enzymatic Activity Assay after Gastric Challenge and the results are presented in Table 3 below.

TABLE 3

Solubilization of arabinoxylan oligomers using xylanase

| Enzyme tested | AHU in dH$_2$O | AHU with 10 mM CaCl$_2$ | AHU with 10 mM NaHCO$_3$ |
|---|---|---|---|
| SEQ ID NO 1 | 41.3$^B$ | 188$^A$ | 176$^A$ |
| SEQ ID NO 2 | 57.8$^B$ | 87.3$^{A,B}$ | 131$^A$ |
| SEQ ID NO 3 | 17.4$^C$ | 68.3$^B$ | 121$^A$ |
| SEQ ID NO 4 | −14.6$^A$ | 5.25$^A$ | 71.8$^A$ |
| Econase XT | 88.6$^A$ | 72.25$^B$ | 67.2$^B$ |

$^{A,B,C}$Means not sharing a common letter are significantly different (TUKEY-Kramer test, p < 0.05).

Example 4: Activity after Gastric Stability of Enzyme Xylanase_A in Presence of Calcium, Carbonate and Oil The release of xylan oligomers from DFDS maize of the xylanase of the invention (SEQ ID NO: 1) was determined using the Enzymatic Activity Assay after Gastric Challenge and the results are presented in Table 5 below.

TABLE 5

Solubilization of arabinoxylan oligomers using xylanase (SEQ. ID NO: 1)

| Enzyme tested | AHU in dH$_2$O | AHU with 10 mM CaCl$_2$ | AHU with 10 mM NaHCO$_3$ | AHU with 2% v/v sunflower oil |
|---|---|---|---|---|
| SEQ. ID NO: 1 | 41.3$^B$ | 187.8$^A$ | 176.3$^A$ | 32.5$^B$ |

$^{A,B}$Means not sharing a common letter are significantly different (TUKEY-Kramer test, p < 0.05).

The invention claimed is:

1. A composition, comprising i) a GH30 xylanase and ii) one or more sources of calcium and/or carbonate, said one or more sources of calcium and/or carbonate present in an amount sufficient to increase solubilization of arabinoxylan oligomers, as compared to a control composition devoid of said one or more sources of calcium and/or carbonate, as measured by the release of xylan oligomers as evaluated by measuring the florescence of a supernatant with excitation at 320 nm and emission at 440 nm with activity of said GH30 xylanase measured in arabinoxylan hydrolyzing unit, said GH30 xylanase comprising a polypeptide having at least 90% sequence identity to SEQ ID NO 1, SEQ ID NO 2, SEQ ID NO 3, SEQ ID NO 16, SEQ ID NO 17, SEQ ID NO 18, SEQ ID NO 19, SEQ ID NO 20 and/or SEQ ID NO 21.

2. The composition of claim 1, said one or more sources of calcium and/or carbonate comprising one or more sources of calcium.

3. The composition of claim 1, said one or more sources of calcium and/or carbonate comprising one or more sources of carbonate.

4. The composition of claim 1, said one or more sources of calcium and/or carbonate comprising calcium chloride, calcium phosphate, tricalcium citrate, calcium lactate, calcium lactate gluconate, calcium carbonate, calcium citrate, calcium malate, calcium glubionate, calcium gluceptate, calcium gluconate and/or calcium acetate.

5. The composition of claim 1, said one or more sources of calcium and/or carbonate comprising calcium chloride.

6. The composition of claim 1, said one or more sources of calcium and/or carbonate comprising calcium carbonate.

7. The composition of claim 1, said one or more sources of calcium and/or carbonate comprising $NaHCO_3$, $Na_2CO_3$, $LiHCO_3$, $KHCO_3$, $CaCO_3$, $Ca(HCO_3)_2$, $BaCO_3$, $FeCO_3$, $ZnCO_3$, $NH_4HCO_3$ and/or $(NH_4)_2CO_3$.

8. The composition of claim 1, said one or more sources of calcium and/or carbonate comprising $NaHCO_3$, $LiHCO_3$ and/or $KHCO_3$.

9. The composition of claim 1, said one or more sources of calcium and/or carbonate comprising $NaHCO_3$.

10. The composition of claim 1, said GH30 xylanase comprising a mature GH30 xylanase from *Bacillus subtilis*.

11. The composition of claim 1, said GH30 xylanase comprising a mature GH30 xylanase from *Bacillus amyloliquefaciens*.

12. The composition of claim 1, said GH30 xylanase comprising a mature GH30 xylanase from *Bacillus licheniformis*.

13. The composition of claim 1, said GH30 xylanase comprising a mature GH30 xylanase from *Paenibacillus pabuli*.

14. The composition of claim 1, said GH30 xylanase comprising a polypeptide having at least 93% sequence identity to SEQ ID NO 1, SEQ ID NO 2, SEQ ID NO 3, SEQ ID NO 16, SEQ ID NO 17, SEQ ID NO 18, SEQ ID NO 19, SEQ ID NO 20 and/or SEQ ID NO 21.

15. The composition of claim 1, said GH30 xylanase comprising a polypeptide having at least 97% sequence identity to SEQ ID NO 1, SEQ ID NO 2, SEQ ID NO 3, SEQ ID NO 16, SEQ ID NO 17, SEQ ID NO 18, SEQ ID NO 19, SEQ ID NO 20 and/or SEQ ID NO 21.

16. The composition of claim 1, said GH30 xylanase comprising a polypeptide having 100% sequence identity to SEQ ID NO 1, SEQ ID NO 2, SEQ ID NO 3, SEQ ID NO 16, SEQ ID NO 17, SEQ ID NO 18, SEQ ID NO 19, SEQ ID NO 20 or SEQ ID NO 21.

17. The composition of claim 1, said GH30 xylanase comprising a polypeptide having at least 95% sequence identity to SEQ ID NO 1, SEQ ID NO 2, SEQ ID NO 3, SEQ ID NO 16, SEQ ID NO 17, SEQ ID NO 18, SEQ ID NO 19, SEQ ID NO 20 and/or SEQ ID NO 21.

18. The composition of claim 1, said GH30 xylanase comprising a polypeptide having at least 99% sequence identity to SEQ ID NO 1, SEQ ID NO 2, SEQ ID NO 3, SEQ ID NO 16, SEQ ID NO 17, SEQ ID NO 18, SEQ ID NO 19, SEQ ID NO 20 and/or SEQ ID NO 21.

19. The composition of claim 1, characterized in that it further comprises one or more animal feed ingredients selected from the group consisting of vitamins, minerals, enzymes, direct fed microbials, amino acids and forage.

20. A method, comprising contacting plant material with the composition of claim 1.

* * * * *

SEQUENCE LISTING

<160> NUMBER OF SEQ ID NOS: 21

<210> SEQ ID NO 1
<211> LENGTH: 391
<212> TYPE: PRT
<213> ORGANISM: Bacillus subtilis
<220> FEATURE:
<221> NAME/KEY: PEPTIDE
<222> LOCATION: (1)..(391)

<400> SEQUENCE: 1

Ala Ala Ser Asp Val Thr Val Asn Val Ser Ala Glu Lys Gln Val Ile
1               5                   10                  15

Arg Gly Phe Gly Gly Met Asn His Pro Ala Trp Ala Gly Asp Leu Thr
            20                  25                  30

Ala Ala Gln Arg Glu Thr Ala Phe Gly Asn Gly Asn Gln Asn Leu Gly
        35                  40                  45

Phe Ser Ile Leu Arg Ile His Val Asp Glu Asn Arg Asn Asn Trp Tyr
50                  55                  60

Lys Glu Val Glu Thr Ala Lys Ser Ala Val Lys His Gly Ala Ile Val
65                  70                  75                  80

Phe Ala Ser Pro Trp Asn Pro Pro Ser Asp Met Val Glu Thr Phe Asn
                85                  90                  95

Arg Asn Gly Asp Thr Ser Ala Lys Arg Leu Lys Tyr Asn Lys Tyr Ala
            100                 105                 110

Ala Tyr Ala Gln His Leu Asn Asp Phe Val Thr Phe Met Lys Asn Asn
        115                 120                 125

Gly Val Asn Leu Tyr Ala Ile Ser Val Gln Asn Glu Pro Asp Tyr Ala
130                 135                 140

His Glu Trp Thr Trp Trp Thr Pro Gln Glu Ile Leu Arg Phe Met Arg
145                 150                 155                 160

Glu Asn Ala Gly Ser Ile Asn Ala Arg Val Ile Ala Pro Glu Ser Phe
                165                 170                 175

Gln Tyr Leu Lys Asn Leu Ser Asp Pro Ile Leu Asn Asp Pro Gln Ala
            180                 185                 190

Leu Ala Asn Met Asp Ile Leu Gly Thr His Leu Tyr Gly Thr Gln Val
        195                 200                 205

Ser Gln Phe Pro Tyr Pro Leu Phe Lys Gln Lys Gly Ala Gly Lys Asp
210                 215                 220

Leu Trp Met Thr Glu Val Tyr Tyr Pro Asn Ser Asp Thr Asn Ser Ala
225                 230                 235                 240

Asp Arg Trp Pro Glu Ala Leu Asp Val Ser Gln His Ile His Asn Ala
                245                 250                 255

Met Val Glu Gly Asp Phe Gln Ala Tyr Val Trp Trp Tyr Ile Arg Arg
            260                 265                 270

Ser Tyr Gly Pro Met Lys Glu Asp Gly Thr Ile Ser Lys Arg Gly Tyr
        275                 280                 285

Asn Met Ala His Phe Ser Lys Phe Val Arg Pro Gly Tyr Val Arg Ile
290                 295                 300

Asp Ala Thr Lys Asn Pro Asn Ala Asn Val Tyr Val Ser Ala Tyr Lys
305                 310                 315                 320

Gly Asp Asn Lys Val Ile Val Ala Ile Asn Lys Ser Asn Thr Gly
                325                 330                 335

Val Asn Gln Asn Phe Val Leu Gln Asn Gly Ser Ala Ser Asn Val Ser
            340                 345                 350

Arg Trp Ile Thr Ser Ser Ser Asn Leu Gln Pro Gly Thr Asn Leu
        355                 360                 365

Thr Val Ser Gly Asn His Phe Trp Ala His Leu Pro Ala Gln Ser Val
370                 375                 380

Thr Thr Phe Val Val Asn Arg
385                 390

<210> SEQ ID NO 2
<211> LENGTH: 391
<212> TYPE: PRT
<213> ORGANISM: Bacillus subtilis

<400> SEQUENCE: 2

```
Ala Ala Asn Asp Val Thr Val Asn Ile Ser Ala Glu Lys Gln Val Ile
1               5                   10                  15

Arg Gly Phe Gly Gly Met Asn His Pro Ala Trp Val Gly Asp Leu Thr
            20                  25                  30

Ala Ala Gln Arg Glu Thr Ala Phe Gly Asn Gly Gln Asn Gln Leu Gly
        35                  40                  45

Phe Ser Ile Leu Arg Ile His Val Asp Glu Asn Arg Asn Asn Trp Tyr
    50                  55                  60

Lys Glu Val Glu Thr Ala Lys Ser Ala Ile Lys His Gly Ala Ile Val
65                  70                  75                  80

Phe Ala Ser Pro Trp Asn Pro Ser Asn Met Val Glu Thr Phe Asn
                85                  90                  95

His Asn Gly Asp Thr Ser Ala Lys Arg Leu Arg Tyr Asp Lys Tyr Ala
            100                 105                 110

Ala Tyr Ala Gln His Leu Asn Asp Phe Val Thr Phe Met Lys Ser Asn
        115                 120                 125

Gly Val Asn Leu Tyr Ala Ile Ser Ile Gln Asn Glu Pro Asp Tyr Ala
    130                 135                 140

His Glu Trp Thr Trp Thr Pro Gln Glu Ile Leu Arg Phe Met Arg
145                 150                 155                 160

Glu Asn Ala Gly Ser Ile Asn Ala Arg Val Ile Ala Pro Glu Ser Phe
                165                 170                 175

Gln Tyr Leu Lys Asn Leu Ser Asp Pro Ile Leu Asn Asp Pro Gln Ala
            180                 185                 190

Leu Ala Asn Met Asp Ile Leu Gly Thr His Leu Tyr Gly Thr Gln Val
        195                 200                 205

Ser Gln Phe Pro Tyr Pro Leu Phe Lys Gln Lys Gly Ala Gly Lys Asp
    210                 215                 220

Leu Trp Met Thr Glu Val Tyr Tyr Pro Asn Ser Asp Asn Asn Ser Ala
225                 230                 235                 240

Asp Arg Trp Pro Glu Ala Leu Asp Val Ser Gln His Ile His Asn Ser
                245                 250                 255

Met Val Glu Gly Asp Phe Gln Ala Tyr Val Trp Trp Tyr Ile Arg Arg
            260                 265                 270

Ser Tyr Gly Pro Met Lys Glu Asp Gly Thr Ile Ser Lys Arg Gly Tyr
        275                 280                 285

Asn Met Ala His Phe Ser Lys Phe Val Arg Pro Gly Tyr Val Arg Ile
    290                 295                 300

Asp Ala Thr Lys Asn Pro Asn Pro Asn Val Tyr Val Ser Ala Tyr Lys
305                 310                 315                 320

Gly Asp Asn Lys Val Val Ile Val Ala Ile Asn Lys Ser Asn Thr Gly
                325                 330                 335

Val Asn Gln Asn Phe Val Leu Gln Asn Gly Ser Ala Ser Gln Val Ser
            340                 345                 350

Arg Trp Ile Thr Ser Ser Asn Ser Asn Leu Gln Pro Gly Thr Asn Leu
        355                 360                 365

Lys Val Thr Asp Asn His Phe Trp Ala His Leu Pro Ala Gln Ser Val
    370                 375                 380

Thr Thr Phe Val Val Ile Arg
385                 390
```

<210> SEQ ID NO 3

```
<211> LENGTH: 392
<212> TYPE: PRT
<213> ORGANISM: Bacillus subtilis
<220> FEATURE:
<221> NAME/KEY: PEPTIDE
<222> LOCATION: (1)..(391)

<400> SEQUENCE: 3
```

| | | | | | | | | | | | | | | |
|---|---|---|---|---|---|---|---|---|---|---|---|---|---|---|
| Ala | Ala | Ser | Asp | Ala | Thr | Val | Arg | Leu | Ser | Ala | Glu | Lys | Gln | Val | Ile |
| 1 | | | | 5 | | | | | 10 | | | | | 15 |
| Arg | Gly | Phe | Gly | Gly | Met | Asn | His | Pro | Ala | Trp | Ile | Gly | Asp | Leu | Thr |
| | | | 20 | | | | | 25 | | | | | 30 | | |
| Ala | Ala | Gln | Arg | Glu | Thr | Ala | Phe | Gly | Asn | Gly | Gln | Asn | Gln | Leu | Gly |
| | | | 35 | | | | | 40 | | | | | 45 | | |
| Phe | Ser | Ile | Leu | Arg | Ile | His | Val | Asp | Glu | Asn | Arg | Asn | Asn | Trp | Tyr |
| 50 | | | | | 55 | | | | | 60 | | | | | |
| Arg | Glu | Val | Glu | Thr | Ala | Lys | Ser | Ala | Ile | Lys | His | Gly | Ala | Ile | Val |
| 65 | | | | 70 | | | | | 75 | | | | | 80 | |
| Phe | Ala | Ser | Pro | Trp | Asn | Pro | Pro | Ser | Asp | Met | Val | Glu | Thr | Phe | Asn |
| | | | | 85 | | | | | 90 | | | | | 95 | |
| Arg | Asn | Gly | Asp | Thr | Ser | Ala | Lys | Arg | Leu | Arg | Tyr | Asp | Lys | Tyr | Ala |
| | | | 100 | | | | | 105 | | | | | 110 | | |
| Ala | Tyr | Ala | Lys | His | Leu | Asn | Asp | Phe | Val | Thr | Phe | Met | Lys | Asn | Asn |
| | | 115 | | | | | 120 | | | | | 125 | | | |
| Gly | Val | Asn | Leu | Tyr | Ala | Ile | Ser | Val | Gln | Asn | Glu | Pro | Asp | Tyr | Ala |
| | 130 | | | | | 135 | | | | | 140 | | | | |
| His | Asp | Trp | Thr | Trp | Trp | Thr | Pro | Gln | Glu | Ile | Leu | Arg | Phe | Met | Lys |
| 145 | | | | | 150 | | | | | 155 | | | | | 160 |
| Glu | Asn | Ala | Gly | Ser | Ile | Asn | Ala | Arg | Val | Ile | Ala | Pro | Glu | Ser | Phe |
| | | | | 165 | | | | | 170 | | | | | 175 | |
| Gln | Tyr | Leu | Lys | Asn | Ile | Ser | Asp | Pro | Ile | Val | Asn | Asp | Pro | Lys | Ala |
| | | | 180 | | | | | 185 | | | | | 190 | | |
| Leu | Ala | Asn | Met | Asp | Ile | Leu | Gly | Ala | His | Leu | Tyr | Gly | Thr | Gln | Leu |
| | | 195 | | | | | 200 | | | | | 205 | | | |
| Asn | Asn | Phe | Ala | Tyr | Pro | Leu | Phe | Lys | Gln | Lys | Gly | Ala | Gly | Lys | Asp |
| | 210 | | | | | 215 | | | | | 220 | | | | |
| Leu | Trp | Met | Thr | Glu | Val | Tyr | Tyr | Pro | Asn | Ser | Asp | Asn | His | Ser | Ala |
| 225 | | | | | 230 | | | | | 235 | | | | | 240 |
| Asp | Arg | Trp | Pro | Glu | Ala | Leu | Asp | Val | Ser | His | His | Ile | His | Asn | Ser |
| | | | | 245 | | | | | 250 | | | | | 255 | |
| Met | Val | Glu | Gly | Asp | Phe | Gln | Ala | Tyr | Val | Trp | Trp | Tyr | Ile | Arg | Arg |
| | | | 260 | | | | | 265 | | | | | 270 | | |
| Ser | Tyr | Gly | Pro | Met | Lys | Glu | Asp | Gly | Thr | Ile | Ser | Lys | Arg | Gly | Tyr |
| | | 275 | | | | | 280 | | | | | 285 | | | |
| Asn | Met | Ala | His | Phe | Ser | Lys | Phe | Val | Arg | Pro | Gly | Tyr | Val | Arg | Val |
| | 290 | | | | | 295 | | | | | 300 | | | | |
| Asp | Ala | Thr | Lys | Ser | Pro | Ala | Ser | Asn | Val | Tyr | Val | Ser | Ala | Tyr | Lys |
| 305 | | | | | 310 | | | | | 315 | | | | | 320 |
| Gly | Asp | Asn | Lys | Val | Val | Ile | Val | Ala | Ile | Asn | Lys | Asn | Asn | Ser | Gly |
| | | | | 325 | | | | | 330 | | | | | 335 | |
| Val | Asn | Gln | Asn | Phe | Val | Leu | Gln | Asn | Gly | Ser | Val | Ser | Gln | Val | Ser |
| | | | 340 | | | | | 345 | | | | | 350 | | |
| Arg | Trp | Ile | Thr | Ser | Ser | Ser | Ser | Asn | Leu | Gln | Pro | Gly | Thr | Asn | Leu |
| | | 355 | | | | | 360 | | | | | 365 | | | |
| Asn | Val | Thr | Asp | Asn | His | Phe | Trp | Ala | His | Leu | Pro | Ala | Gln | Ser | Val |

```
                370                 375                 380

Thr Thr Phe Val Ala Asn Leu Arg
385                 390

<210> SEQ ID NO 4
<211> LENGTH: 185
<212> TYPE: PRT
<213> ORGANISM: Bacillus subtilis
<220> FEATURE:
<221> NAME/KEY: PEPTIDE
<222> LOCATION: (1)..(185)

<400> SEQUENCE: 4

Ala Asn Thr Asp Tyr Trp Gln Asn Trp Thr Asp Gly Gly Gly Thr Val
1               5                   10                  15

Asn Ala Val Asn Gly Ser Gly Gly Asn Tyr Ser Val Asn Trp Ser Asn
                20                  25                  30

Thr Gly Asn Phe Val Val Gly Lys Gly Trp Thr Thr Gly Ser Pro Phe
            35                  40                  45

Arg Thr Ile Asn Tyr Asn Ala Gly Val Trp Ala Pro Asn Gly Asn Ala
        50                  55                  60

Tyr Leu Thr Leu Tyr Gly Trp Thr Arg Ser Pro Leu Ile Glu Tyr Tyr
65                  70                  75                  80

Val Val Asp Ser Trp Gly Thr Tyr Arg Pro Thr Gly Thr Tyr Lys Gly
                85                  90                  95

Thr Val Tyr Ser Asp Gly Gly Thr Tyr Asp Val Tyr Thr Thr Thr Arg
            100                 105                 110

Tyr Asp Ala Pro Ser Ile Asp Gly Asp Lys Thr Thr Phe Thr Gln Tyr
        115                 120                 125

Trp Ser Val Arg Gln Ser Lys Arg Pro Thr Gly Ser Asn Ala Thr Ile
130                 135                 140

Thr Phe Ser Asn His Val Asn Ala Trp Lys Arg Tyr Gly Met Asn Leu
145                 150                 155                 160

Gly Ser Asn Trp Ser Tyr Gln Val Leu Ala Thr Glu Gly Tyr Arg Ser
                165                 170                 175

Ser Gly Ser Ser Asn Val Thr Val Trp
            180                 185

<210> SEQ ID NO 5
<211> LENGTH: 185
<212> TYPE: PRT
<213> ORGANISM: Bacillus subtilis
<220> FEATURE:
<221> NAME/KEY: PEPTIDE
<222> LOCATION: (1)..(185)

<400> SEQUENCE: 5

Ala Ser Thr Asp Tyr Trp Gln Asn Trp Thr Asp Gly Gly Gly Ile Val
1               5                   10                  15

Asn Ala Val Asn Gly Ser Gly Gly Asn Tyr Ser Val Asn Trp Ser Asn
                20                  25                  30

Thr Gly Asn Phe Val Val Gly Lys Gly Trp Thr Thr Gly Ser Pro Phe
            35                  40                  45

Arg Thr Ile Asn Tyr Asn Ala Gly Val Trp Ala Pro Asn Gly Asn Gly
        50                  55                  60

Tyr Leu Thr Leu Tyr Gly Trp Thr Arg Ser Pro Leu Ile Glu Tyr Tyr
65                  70                  75                  80

Val Val Asp Ser Trp Gly Thr Tyr Arg Pro Thr Gly Thr Tyr Lys Gly
```

```
                        85                  90                  95
Thr Val Lys Ser Asp Gly Gly Thr Tyr Asp Ile Tyr Thr Thr Thr Arg
                100                 105                 110

Tyr Asn Ala Pro Ser Ile Asp Gly Asp Arg Thr Thr Phe Thr Gln Tyr
                115                 120                 125

Trp Ser Val Arg Gln Ser Lys Arg Pro Thr Gly Ser Asn Ala Thr Ile
    130                 135                 140

Thr Phe Ser Asn His Val Asn Ala Trp Lys Ser His Gly Met Asn Leu
145                 150                 155                 160

Gly Ser Asn Trp Ala Tyr Gln Val Met Ala Thr Glu Gly Tyr Gln Ser
                165                 170                 175

Ser Gly Ser Ser Asn Val Thr Val Trp
                180                 185

<210> SEQ ID NO 6
<211> LENGTH: 557
<212> TYPE: PRT
<213> ORGANISM: Clostridium acetobutylicum
<220> FEATURE:
<221> NAME/KEY: mat_peptide
<222> LOCATION: (1)..(557)

<400> SEQUENCE: 6

Ala Ser Asn Val Met Val Asn Leu Ala Ser Lys Lys Gln Val Ile Arg
1               5                   10                  15

Gly Phe Gly Gly Met Asn Ser Val Ala Trp Ala Gly Asp Leu Thr Ala
                20                  25                  30

Ala Gln Arg Glu Thr Ala Phe Gly Asn Gly Asn Gln Leu Gly Leu
            35                  40                  45

Ser Val Val Arg Ile Phe Val Asp Asp Asn Lys Asn Trp Tyr Lys
    50                  55                  60

Glu Leu Pro Thr Ala Lys Ser Ala Ile Ala His Gly Ser Ile Val Phe
65                  70                  75                  80

Ala Thr Pro Trp Asn Pro Pro Ser Ser Met Thr Glu Thr Phe Asn Arg
                85                  90                  95

Asn Gly Glu Lys Ala Lys Arg Leu Arg Tyr Asp Lys Tyr Gly Asp Tyr
                100                 105                 110

Ala Lys Tyr Leu Asn Asp Phe Val Ser Tyr Met Lys Asn Asn Gly Val
            115                 120                 125

Asn Leu Tyr Ala Ile Ser Val Gln Asn Glu Pro Asp Tyr Gly Arg Asp
    130                 135                 140

Trp Thr Trp Trp Thr Pro Gln Glu Val Leu Arg Phe Met Arg Asp Tyr
145                 150                 155                 160

Ala Gly Ser Ile Asn Cys Arg Val Met Ser Pro Glu Ser Phe Ser Tyr
                165                 170                 175

Gln Lys Asn Met Tyr Asp Pro Ile Leu Asn Asp Pro Lys Ala Leu Ala
            180                 185                 190

Asn Met Asp Ile Leu Gly Thr His Thr Tyr Gly Thr Gln Val Lys Asp
    195                 200                 205

Phe Pro Tyr Pro Leu Phe Lys Gln Lys Ala Ala Gly Lys Asp Leu Trp
210                 215                 220

Met Thr Glu Val Tyr Val Pro Asn Ser Asp Ala Asn Ser Ala Asp Arg
225                 230                 235                 240

Trp Pro Glu Ala Leu Glu Val Ala Asn His Ile Asn Asn Ala Met Val
                245                 250                 255
```

Glu Gly Asp Phe Gln Ala Tyr Val Trp Trp Tyr Ile Arg Arg Ser Tyr
            260                 265                 270

Gly Leu Ile Lys Glu Asn Gly Ala Ile Ser Lys Arg Gly Tyr Met Met
        275                 280                 285

Ala His Phe Ser Lys Phe Val Arg Pro Gly Tyr Val Arg Val Asp Ala
    290                 295                 300

Thr Lys Asn Pro Val Gly Asn Val Tyr Val Ser Ala Tyr Thr Gly Asn
305                 310                 315                 320

Asn Lys Val Val Ile Val Ala Ile Asn Lys Gly Thr Tyr Pro Val Asn
                325                 330                 335

Gln Ser Phe Asn Ile Gln Asn Ser Thr Val Ser Asn Val Ser Ser Trp
            340                 345                 350

Val Thr Ser Gly Thr Leu Asn Met Ala Lys Thr Asn Ser Asn Ile Asn
        355                 360                 365

Ala Ala Asn Gly Arg Phe Asn Ala Ser Leu Pro Ala Gln Ser Val Thr
    370                 375                 380

Thr Phe Val Ala Asp Leu Asn Ser Thr Lys Pro Thr Thr Asn Pro Thr
385                 390                 395                 400

Thr Asn Pro Thr Pro Gly Ser Thr Val Thr Leu Asn Asn Gly Trp Tyr
                405                 410                 415

Tyr Ile Lys Asn Ile Asn Ala Gln Lys Tyr Leu Gln Val Ala Asn Asn
            420                 425                 430

Thr Gly Lys Ala Gly Gln Asn Val Glu Leu Gly Ser Gly Ser Gly Val
        435                 440                 445

Ala Gly Gln Lys Trp Tyr Leu Thr Asn Thr Gly Asp Gly Tyr Ile Thr
    450                 455                 460

Leu Lys Asn Ala Leu Gly Asn Tyr Met Leu Asp Val Ser Tyr Gly Glu
465                 470                 475                 480

Asn Lys Asp Gly Ser Asn Ile Gln Ile Phe Asn Ala Tyr Ser Gly Asp
                485                 490                 495

Ser Gln Lys Phe Ala Val Lys Ala Ser Ser Lys Asn Gly Gln Tyr Ser
            500                 505                 510

Val Ala Thr Lys Ser Ser Asn Gly Ser Lys Val Leu Asp Asp Tyr Asn
        515                 520                 525

Phe Gly Thr Ala Asp Gly Thr Asn Val Cys Gln Trp Thr Tyr Gly Gly
    530                 535                 540

Asn Ala Asn Gln Leu Trp Val Phe Glu Pro Thr Asn Asn
545                 550                 555

<210> SEQ ID NO 7
<211> LENGTH: 382
<212> TYPE: PRT
<213> ORGANISM: Pseudoalteromonas tetraodonis
<220> FEATURE:
<221> NAME/KEY: mat_peptide
<222> LOCATION: (1)..(382)

<400> SEQUENCE: 7

Ser Asn Val Thr Ile Asn Phe Asn Thr Gln Tyr Gln Gln Ile Asp Gly
1               5                   10                  15

Phe Gly Gly Met Asn Ala Pro Gly Trp Ile Asn Asp Leu Thr Pro Ala
            20                  25                  30

Gln Ala Thr Lys Ala Phe Gly Thr Gly Asn Gly Glu Met Gly Leu Ser
        35                  40                  45

Ile Met Arg Met Arg Ile Ala Pro Asp Ser Asn Gln Trp Tyr Lys Gln
    50                  55                  60

Val Pro Thr Ala Lys Ile Ala Lys Ser Tyr Gly Ala Lys Leu Leu Ala
65                  70                  75                  80

Ser Pro Trp Ser Pro Ala Tyr Met Lys Ser Asn Asn Asn Leu Asn
            85                  90                  95

Asn Gly Gly Lys Leu Glu Lys Thr His Tyr Trp Gly Tyr Thr Asn His
            100                 105                 110

Leu Met Asp Phe Thr Asn Tyr Met Ala Ser Gln Gly Ala Ser Val Tyr
            115                 120                 125

Ala Leu Ser Leu Gln Asn Glu Pro Asp Trp His Pro Glu Tyr Glu Ser
130                 135                 140

Cys Asp Trp Ser Ala Ser Asp Phe Val Asn Tyr Leu Asn Asp Gln Gly
145                 150                 155                 160

Trp Arg Leu Asp Pro Ala Leu Lys Ile Leu Ala Pro Glu Ser Leu Gly
                165                 170                 175

Phe Asn Lys Ala Leu Ser Asp Pro Ile Leu Asn Asn Ser Val Ala Asn
            180                 185                 190

Asn Tyr Val Asp Ile Ile Gly Gly His Leu Tyr Gly Val Ser Pro Ser
            195                 200                 205

Asn Tyr Pro Leu Ala Leu Gln Lys Gly Lys Lys Leu Trp Met Thr Glu
210                 215                 220

His Tyr Thr Asp Asn Glu Asp Gly Asn Asn Trp Asn Ala Ser Ile Asp
225                 230                 235                 240

Val Gly Leu Glu Leu His Gln Ser Met Val Ser Asn Tyr Ser Ala Tyr
                245                 250                 255

Ile Trp Trp Tyr Ile Arg Arg Ser Tyr Gly Leu Met Ser Glu Asp Gly
            260                 265                 270

Asn Val Ser Lys Arg Gly Tyr Ile Met Ala Gln Phe Ser Lys Tyr Ile
            275                 280                 285

Arg Pro Gly Tyr Thr Arg Ile Gly Ala Thr Glu Met Pro Glu Asn Asn
            290                 295                 300

Val Tyr Val Thr Ala Tyr Lys Asn Asn Ala Gly Lys Leu Val Ile Val
305                 310                 315                 320

Val Val Asn Lys Ser Gly Ser Pro Lys Ala Leu Asp Phe Thr Leu Gln
                325                 330                 335

Asn Gly Thr Val Asn Thr Leu Thr Lys Tyr Ser Thr Ser Ala Ser Met
            340                 345                 350

Asn Met Glu Tyr Arg Gly Lys Ser Thr Val Ser Asn Asn Arg Phe Ser
            355                 360                 365

Ala Tyr Ala Asp Ala Trp Ala Val Gln Thr Phe Val Ser Asn
            370                 375                 380

<210> SEQ ID NO 8
<211> LENGTH: 391
<212> TYPE: PRT
<213> ORGANISM: Paenibacillus species
<220> FEATURE:
<221> NAME/KEY: mat_peptide
<222> LOCATION: (1)..(391)

<400> SEQUENCE: 8

Ala Ser Asp Ala Ile Val Asn Ile Ser Ala Glu Lys Gln Val Ile Arg
1               5                   10                  15

Gly Phe Gly Gly Ile Asn His Pro Val Trp Ile Gly Asp Leu Thr Ala
            20                  25                  30

Ala Gln Arg Glu Thr Ala Phe Gly Asn Gly Asn Asn Gln Leu Gly Phe

```
                35                  40                  45
Ser Ile Leu Arg Ile Tyr Val His Glu Asp Arg Asn Gln Trp Tyr Arg
 50                  55                  60

Glu Val Glu Thr Ala Lys Arg Ala Ile Ala Leu Gly Ala Ile Val Phe
 65                  70                  75                  80

Ala Ser Pro Trp Asn Pro Pro Ala Asp Met Val Glu Thr Phe Asn Arg
                 85                  90                  95

Asn Gly Asp Pro Ser Ala Lys Arg Leu Arg Tyr Asp Lys Tyr Ala Ala
                100                 105                 110

Tyr Ala Gln His Leu Asn Asp Phe Val Thr Tyr Met Arg Asn Asn Gly
            115                 120                 125

Val Asn Leu Tyr Ala Ile Ser Val Gln Asn Glu Pro Asp Tyr Ala His
        130                 135                 140

Asp Trp Thr Trp Trp Thr Pro Gln Glu Met Leu Arg Phe Met Lys Glu
145                 150                 155                 160

Asn Ala Gly Ser Ile Asn Thr Arg Val Ile Ala Pro Glu Ser Phe Gln
                165                 170                 175

Tyr Leu Lys Asn Met Ser Asp Pro Ile Leu Asn Asp Pro Gln Ala Leu
            180                 185                 190

Ala Asn Met Asp Ile Leu Gly Ala His Leu Tyr Gly Thr Gln Val Ser
        195                 200                 205

Asn Phe Ala Tyr Pro Leu Phe Lys Gln Lys Gly Ala Gly Lys Asp Leu
    210                 215                 220

Trp Met Thr Glu Val Tyr Tyr Pro Asn Ser Asp Asn Ser Ala Asp
225                 230                 235                 240

Arg Trp Pro Glu Ala Leu Asp Val Ser Tyr His Ile His Asn Ala Met
                245                 250                 255

Val Glu Gly Asp Phe Gln Ala Tyr Val Trp Trp Tyr Ile Arg Arg Ser
            260                 265                 270

Tyr Gly Pro Met Lys Glu Asp Gly Thr Ile Ser Lys Arg Gly Tyr Ala
        275                 280                 285

Met Ala His Phe Ser Lys Phe Val Arg Pro Gly Tyr Val Arg Val Glu
    290                 295                 300

Ala Thr Lys Asn Pro Glu Thr Asn Val Tyr Val Ser Ala Tyr Lys Gly
305                 310                 315                 320

Asn Lys Lys Leu Val Ile Val Ala Val Asn Lys Asn Ser Gly Val
                325                 330                 335

Asn Gln Asn Phe Val Leu Pro Asn Ala Ser Val Ser Lys Ile Ser Arg
            340                 345                 350

Trp Ile Thr Ser Gly Ser Ser Asn Leu Gln Pro Gly Thr Glu Leu Thr
        355                 360                 365

Met Thr Gly Gly Asn Phe Trp Ala His Leu Pro Ala Gln Ser Val Thr
    370                 375                 380

Thr Phe Val Ala Asp Leu Gly
385                 390

<210> SEQ ID NO 9
<211> LENGTH: 383
<212> TYPE: PRT
<213> ORGANISM: Pectobacterium carotovorum
<220> FEATURE:
<221> NAME/KEY: mat_peptide
<222> LOCATION: (1)..(383)

<400> SEQUENCE: 9
```

Asp Thr Val Lys Ile Asp Ala Lys Thr Ser Tyr Gln Ile Ile Gln Gly
1               5                   10                  15

Phe Gly Gly Met Asn Ala Pro Gly Trp Ile Asn Asp Leu Thr Thr Glu
            20                  25                  30

Gln Val Asn Thr Ala Phe Gly Asn Asp Thr Gly Gln Ile Gly Leu Ser
        35                  40                  45

Ile Met Arg Met Arg Ile Asp Pro Asp Ala Asn Arg Trp Asn Ile Gln
50                  55                  60

Val Ser Ser Ala Arg Gln Ala Ser Leu Leu Gly Ala Lys Leu Met Ala
65                  70                  75                  80

Thr Pro Trp Thr Pro Pro Ala Tyr Met Lys Ser Asn Lys Ser Leu Ile
                85                  90                  95

Asn Gly Gly Arg Leu Leu Ser Glu His Tyr Ser Gly Tyr Thr Glu His
            100                 105                 110

Leu Leu Lys Phe Ser Asn Phe Met Gln Thr Asn Asn Ala Pro Leu Tyr
        115                 120                 125

Ala Ile Ser Ile Gln Asn Glu Pro Asp Trp Lys Pro Asp Tyr Glu Ser
130                 135                 140

Cys Glu Trp Asn Gly Asn Asp Phe Lys Asn Tyr Leu Lys Ser Gln Gly
145                 150                 155                 160

Ser Lys Phe Gly Ser Leu Lys Val Ile Val Gly Glu Ser Leu Asn Phe
                165                 170                 175

Asn His Ser Leu Thr Asp Pro Thr Leu Asn Asp Ser Glu Ala Ala Lys
            180                 185                 190

His Val Ala Ile Val Gly Gly His Leu Tyr Gly Thr Thr Pro Lys Pro
        195                 200                 205

Tyr Pro Leu Ala Gln Asn Lys Gly Lys Glu Val Trp Met Thr Glu His
210                 215                 220

Leu Val Asp Ser Lys Gln Ser Ala Asn Asn Trp Ser Ser Ala Leu Glu
225                 230                 235                 240

Val Ala Ser Glu Met Asn Ala Ser Met Val Ala Asn Tyr Asn Ala Tyr
                245                 250                 255

Val Trp Trp Tyr Ile Arg Arg Ser Tyr Gly Leu Leu Thr Glu Asp Gly
            260                 265                 270

Lys Val Ser Lys Arg Gly Tyr Val Met Ala Gln Tyr Ala Lys Phe Val
        275                 280                 285

Arg Pro Gly Phe Gln Arg Ile Gln Ala Thr Glu Asn Pro Gln Ala Asn
290                 295                 300

Val His Leu Thr Ala Tyr Lys Asn Ser Glu Gly Lys Met Val Ile Val
305                 310                 315                 320

Ala Ile Asn Thr Asn Asp Ser Asp Gln Leu Leu Ser Leu Asn Ile Ser
                325                 330                 335

Asn His Thr Val Ser Lys Phe Glu Lys Tyr Ser Thr Ser Ala Ile Leu
            340                 345                 350

Asn Val Glu Tyr Gly Gly Thr Tyr Lys Val Asp Ser Asn Gly Lys Ser
        355                 360                 365

Ser Val Trp Leu Asn Pro Leu Ser Val Thr Thr Phe Val Gly Lys
370                 375                 380

<210> SEQ ID NO 10
<211> LENGTH: 565
<212> TYPE: PRT
<213> ORGANISM: Ruminococcus species
<220> FEATURE:
<221> NAME/KEY: mat_peptide

<222> LOCATION: (1)..(565)

<400> SEQUENCE: 10

```
Ala Asp Val Cys Val Ile Asp Thr Asp Thr Glu His Gln Met Ile Arg
1               5                   10                  15

Gly Phe Gly Gly Ile Asn His Pro Glu Trp Ala Gly Asp Leu Thr Gln
            20                  25                  30

Ala Gln Arg Gln Thr Ala Phe Gly Asn Gly Glu Asn Glu Leu Gly Leu
        35                  40                  45

Thr Val Leu Arg Val Phe Val Asn Pro Asp Ser Ser Gln Trp Ser Arg
    50                  55                  60

Ala Leu Pro Thr Ala Gln Phe Ala Thr Gln Met Gly Val Thr Val Phe
65                  70                  75                  80

Ala Ser Pro Trp Glu Pro Pro Ala Asn Leu Thr Glu Ser Gly Gly Ser
                85                  90                  95

Asn Gly Lys Leu His Leu Pro Lys Ser Asn Tyr Ala Ala Tyr Ala Lys
            100                 105                 110

His Leu Asn Asp Phe Gly Thr Tyr Met Lys Asn Asn Val Asp Leu
        115                 120                 125

Tyr Ala Ile Ser Val Gln Asn Glu Pro Asp Tyr Ala Ser Glu Trp Thr
    130                 135                 140

Tyr Trp Ser Thr Asp Glu Thr Thr Asp Phe Ile Ala Asn Tyr Gly Asp
145                 150                 155                 160

Gln Ile Thr Ser Thr Arg Leu Met Ser Pro Glu Ser Phe Gln Tyr Ala
                165                 170                 175

Pro Glu Asn Ala Ser Trp Val Ser Asp Gly Gly Lys Lys Phe Tyr Arg
            180                 185                 190

Lys Ile Leu Asn Asn Ser Lys Ala Met Ala Asn Cys Asp Val Phe Gly
        195                 200                 205

Thr His Phe Tyr Gly Thr Gln Arg Ser Trp Met Asp Phe Pro Asp Leu
    210                 215                 220

Glu Asn Ser Gly Lys Glu Ile Trp Met Thr Glu Val Tyr Val Pro Asn
225                 230                 235                 240

Ser Asp Lys Asp Ser Ala Asn Arg Tyr Pro Glu Ala Leu Gln Val Ser
                245                 250                 255

Glu Asn Ile His Asn Ala Met Val Val Gly Asn Met Ser Ala Tyr Thr
            260                 265                 270

Trp Trp Tyr Ile Arg Arg Asn Tyr Gly Leu Met Thr Glu Asp Gly Lys
        275                 280                 285

Ile Ser Lys Arg Gly Tyr Cys Met Ala Gln Tyr Ser Lys Tyr Val Arg
    290                 295                 300

Pro Gly Asp Val Arg Ile Asp Ala Thr Glu Gln Pro Ala Asp Asn Val
305                 310                 315                 320

Tyr Val Ser Ala Tyr Lys Gly Asp Asp Asn Gln Val Thr Ile Val Ala
                325                 330                 335

Ile Asn Lys Gly Thr Glu Ser Tyr Ser Gln Gln Phe Ala Val Asp Ala
            340                 345                 350

Asp Ala Gln Ile Thr Glu Val Asp Arg Tyr Arg Thr Ser Ala Ser Glu
        355                 360                 365

Asn Leu Ala Lys Thr Glu Asn Met Glu His Asp Ser Ser Ser Phe Trp
    370                 375                 380

Ala Gln Leu Pro Ala Glu Ser Val Ser Thr Phe Val Val Thr Leu Glu
385                 390                 395                 400
```

```
Asp Gln Pro Val Glu Pro Asp Glu Asn Gly Tyr Tyr Phe His Asp Thr
                405                 410                 415

Phe Glu Ser Asp Asn Cys Asp Trp Gln Gly His Gly Ser Ala Asp Ile
            420                 425                 430

Thr Leu Ser Gly Arg Ile Pro Tyr Gln Gly Thr Asn Ala Leu Leu Val
        435                 440                 445

Gln Asn Arg Ala Ser Ala Trp Asn Gly Ala Glu Lys Val Leu Pro Ala
450                 455                 460

Lys Ala Phe Gln Ala Gly Lys Glu Tyr Ser Phe Ser Val Cys Leu Asn
465                 470                 475                 480

Tyr Met Asp Gly Glu Ser Ser Lys Asn Ala Ala Leu Ser Leu Gln Tyr
                485                 490                 495

Thr Asp Ala Ala Gly Glu Thr Lys Tyr Ala Arg Ile Ala Ser Ala Ser
            500                 505                 510

Ala Ala Lys Gly Asn Tyr Val Gln Leu Ala Asn Pro Ser Phe Lys Leu
        515                 520                 525

Pro Asp Gly Gly Lys Asn Phe Lys Ile Tyr Val Glu Thr Glu Gly Asp
530                 535                 540

Thr Asp Asn Phe Tyr Ile Asp Glu Ala Ile Gly Ala Val Lys Gly Thr
545                 550                 555                 560

Ala Ile Glu Gly Pro
                565

<210> SEQ ID NO 11
<211> LENGTH: 396
<212> TYPE: PRT
<213> ORGANISM: Streptomyces species
<220> FEATURE:
<221> NAME/KEY: Streptomyces sp-62627
<222> LOCATION: (1)..(396)

<400> SEQUENCE: 11

Ser Arg Thr Pro Ser Ala Ala Thr Ser Val Thr Val Asp Pro Ser
1               5                   10                  15

Ala Thr Arg Gln Thr Ile Arg Gly Phe Gly Gly Met Asn His Pro Leu
                20                  25                  30

Trp Ile Gly Asp Leu Thr Pro Ala Gln Arg Asp Thr Ala Phe Gly Asn
            35                  40                  45

Gly Glu Gly Gln Leu Gly Phe Ser Val Leu Arg Ile Pro Val Ser Glu
        50                  55                  60

Asp Arg Ala Asn Trp Ser Arg Glu Val Ala Thr Ala Lys Arg Ala Thr
65                  70                  75                  80

Glu Leu Gly Ala Ile Val Phe Ala Ser Pro Trp Asn Pro Pro Ala Asn
                85                  90                  95

Met Val Glu Thr Phe Val Arg Gly Gln Gln Thr Asp Ala Lys Arg Leu
                100                 105                 110

Arg His Ser Met Tyr Gly Ala Tyr Ala Gln His Leu Asn Asp Phe Val
            115                 120                 125

Ala Phe Met Lys Ser Asn Gly Val Asn Leu Tyr Ala Ile Ser Val Gln
        130                 135                 140

Asn Glu Pro Asp Tyr Ala His Asp Trp Thr Trp Thr Pro Ser Glu
145                 150                 155                 160

Met Thr Arg Phe Leu Arg Glu Asn Ala Gly Ser Ile Ser Thr Lys Val
                165                 170                 175

Ile Ala Pro Glu Ser Phe Gln Tyr Val Lys Thr Phe Ser Asp Pro Ile
                180                 185                 190
```

```
Leu Asn Asp Ala Ala Leu Ala Asn Leu Asp Ile Leu Gly Ala His
        195                 200                 205

Leu Tyr Gly Thr Ser Phe Gln Asn Phe Pro Tyr Leu Phe Lys Gln
        210                 215                 220

Lys Gly Gly Lys Glu Leu Trp Met Thr Glu Val Tyr His Pro Asn
225                 230                 235                 240

Ser Ser Asp Ser Ala Asp Leu Trp Pro Gln Ala Leu Asp Val Ala Glu
                245                 250                 255

His Ile His Arg Ala Met Val Asp Ala Glu Phe Gln Ala Tyr Val Trp
                260                 265                 270

Trp Tyr Ile Arg Arg Gly Tyr Gly Pro Met Arg Glu Asp Gly Arg Ile
        275                 280                 285

Ser Lys Arg Gly Ala Gly Met Ala His Phe Ser Lys Phe Val Arg Pro
        290                 295                 300

Gly His Val Arg Val Ala Val Thr Pro Ala Pro Gln Pro Asn Val Tyr
305                 310                 315                 320

Leu Ser Ala Tyr Lys Gly Gly Ser Arg Val Val Val Ala Val
                325                 330                 335

Asn Lys Gly Ala Ser Pro Val Ser Gln Gln Phe Thr Leu Asn Asn Asn
        340                 345                 350

Asn Ser Ser Gly Val Ser Ser Trp Val Thr Asp Ala Ser Arg Asn Leu
        355                 360                 365

Ala Ser Gln Gly Arg Ile Thr Val Ala Asn Gly Ala Phe Thr Ala Arg
        370                 375                 380

Leu Pro Ala Gln Ser Val Thr Thr Leu Val Thr Gly
385                 390                 395

<210> SEQ ID NO 12
<211> LENGTH: 392
<212> TYPE: PRT
<213> ORGANISM: Clostridium saccharoperbutylacetonicum
<220> FEATURE:
<221> NAME/KEY: mat_peptide
<222> LOCATION: (1)..(392)

<400> SEQUENCE: 12

Ala Ser Asn Ala Thr Ile Asn Leu Ser Ala Gln Lys Gln Val Ile Arg
1               5                   10                  15

Gly Phe Gly Gly Ile Asn Leu Pro Ala Trp Ala Gly Asp Leu Thr Ala
            20                  25                  30

Ala Gln Arg Glu Thr Ala Phe Gly Asn Gly Asp Asn Gln Leu Gly Leu
        35                  40                  45

Ser Val Leu Arg Ile Tyr Val Asp Asp Asn Lys Asn Asn Trp Tyr Lys
    50                  55                  60

Glu Leu Ala Thr Ala Lys Lys Ala Ile Glu His Gly Ala Ile Val Phe
65                  70                  75                  80

Ala Thr Pro Trp Asn Pro Pro Ala Tyr Met Thr Glu Lys Phe Asn Arg
                85                  90                  95

Asn Gly Asp Thr Asn Ala Lys Arg Leu Arg Tyr Asp Lys Tyr Ala Ala
            100                 105                 110

Tyr Ala Gln His Leu Asn Asp Phe Val Ser Tyr Met Lys Asn Asn Gly
        115                 120                 125

Val Asn Leu Tyr Ala Ile Ser Val Gln Asn Glu Pro Asp Tyr Gly Lys
    130                 135                 140

Glu Trp Thr Trp Trp Thr Pro Gln Glu Ile Leu Arg Phe Ile Lys Glu
```

-continued

```
            145                 150                 155                 160
    Asn Ala Gly Ser Ile Asn Cys Arg Val Met Ser Pro Glu Ser Phe Ser
                    165                 170                 175

Tyr Gln Lys Asn Met Tyr Asp Pro Ile Leu Asn Asn Pro Gln Ala Leu
                    180                 185                 190

Ala Asn Met Asp Ile Leu Gly Thr His Thr Tyr Gly Thr Arg Val Asn
                    195                 200                 205

Asp Phe Ala Tyr Pro Leu Phe Lys Gln Lys Gly Ala Gly Lys Glu Leu
                    210                 215                 220

Trp Met Thr Glu Val Tyr Val Pro Asn Ser Asp Thr Asn Ser Ala Asp
    225                 230                 235                 240

Arg Trp Pro Glu Ala Leu Asp Val Ala Asp His Ile Asn Asn Ala Met
                    245                 250                 255

Val Glu Gly Asp Phe Gln Ala Tyr Val Trp Trp Tyr Ile Arg Arg Ser
                    260                 265                 270

Tyr Gly Phe Ile Lys Glu Asp Gly Asn Val Ser Lys Arg Gly Tyr Met
                    275                 280                 285

Met Ala His Phe Ser Lys Phe Val Arg Pro Gly Tyr Val Arg Val Asp
                    290                 295                 300

Ala Thr Lys Asn Pro Thr Pro Asn Val Tyr Leu Ser Ala Tyr Lys Gly
    305                 310                 315                 320

Asn Asn Lys Val Val Ile Ile Ala Ile Asn Lys Gly Thr Ser Asp Val
                    325                 330                 335

Lys Gln Ser Phe Thr Met Pro Asn Ser Lys Val Ser Ser Val Ser Ser
                    340                 345                 350

Trp Gln Thr Thr Ala Thr Ala Asn Leu Ala Lys Ser Ala Ser Asn Thr
                    355                 360                 365

Asn Val Tyr Asn Gly Asn Phe Thr Ala Thr Leu Pro Ala Gln Ser Val
                    370                 375                 380

Thr Thr Phe Val Gly Asp Ile Lys
    385                 390

<210> SEQ ID NO 13
<211> LENGTH: 413
<212> TYPE: PRT
<213> ORGANISM: Paenibacillus panacisoli
<220> FEATURE:
<221> NAME/KEY: mat_peptide
<222> LOCATION: (1)..(413)

<400> SEQUENCE: 13

Ala Ser Asp Ala Val Ile Asn Leu Ser Ala Gln Lys Gln Val Ile Arg
    1               5                   10                  15

Gly Phe Gly Gly Ile Asn His Pro Ala Trp Ile Gly Asp Leu Thr Ala
                    20                  25                  30

Ala Gln Arg Glu Thr Ala Phe Gly Asn Gly Gln Asn Gln Leu Gly Phe
                    35                  40                  45

Ser Ile Leu Arg Val Tyr Ile Asp Pro Asp Arg Asn Asn Trp Ser Arg
                    50                  55                  60

Glu Val Ala Thr Ala Lys Lys Ala Ile Glu Lys Gly Ala Leu Val Phe
    65                  70                  75                  80

Ala Ser Pro Trp Asn Pro Pro Ser Ser Met Val Glu Thr Phe Asn Arg
                    85                  90                  95

Asn Gly Asp Arg Asn Ala Lys Arg Leu Arg Tyr Asp Lys Tyr Ala Ala
                    100                 105                 110
```

```
Tyr Ala Gln His Leu Asn Asp Phe Val Thr Tyr Met Lys Asn Asn Gly
            115                 120                 125

Val Asn Leu Tyr Ala Ile Ser Val Gln Asn Glu Pro Asp Tyr Ala His
    130                 135                 140

Glu Trp Thr Trp Trp Thr Pro Gln Glu Ile Leu Arg Phe Met Lys Glu
145                 150                 155                 160

Asn Ala Gly Ser Ile Asn Cys Lys Val Met Ala Pro Glu Ser Phe Gln
                165                 170                 175

Tyr Leu Lys Asn Ile Ser Asp Pro Ile Leu Asn Asp Pro Gln Ala Leu
            180                 185                 190

Ala Asn Met Asp Ile Leu Gly Ala His Leu Tyr Gly Thr Gln Val Ser
    195                 200                 205

Asn Phe Ala Tyr Pro Leu Phe Lys Gln Lys Gly Ala Gly Lys Glu Leu
210                 215                 220

Trp Met Thr Glu Val Tyr Tyr Pro Asn Ser Asp Asn Ser Ala Asp
225                 230                 235                 240

Arg Trp Pro Glu Ala Leu Glu Val Ser His His Met His Asn Ala Met
                245                 250                 255

Val Glu Gly Asp Phe Gln Ala Tyr Val Trp Trp Tyr Ile Arg Arg Ser
            260                 265                 270

Tyr Gly Pro Met Lys Glu Asp Gly Thr Ile Ser Lys Arg Gly Tyr Asn
    275                 280                 285

Met Ala His Phe Ser Lys Phe Ile Arg Pro Gly Tyr Val Arg Val Asp
290                 295                 300

Ala Thr Lys Asn Pro Asp Thr Asn Val His Val Ser Ala Tyr Lys Gly
305                 310                 315                 320

Asn Asn Lys Val Val Ile Val Ala Ile Asn Arg Gly Thr Thr Ala Val
                325                 330                 335

Asn Gln Asn Phe Val Leu Gln Asn Gly Arg Ala Ala Thr Leu Ser Arg
            340                 345                 350

Trp Ile Thr Asp Ala Asn Arg Asn Leu Ala Pro Glu Ser Asn Leu Asn
    355                 360                 365

Ala Ser Ser Gly Ser Phe Phe Ala His Leu Pro Ala Lys Ser Val Thr
370                 375                 380

Thr Phe Val Gly Asp Leu Thr Gly Ser Thr Leu Asn Ile Glu Asp Ala
385                 390                 395                 400

Ala Leu Thr Asn Ser Val Thr Gln Asp Thr Tyr Ser Lys
                405                 410

<210> SEQ ID NO 14
<211> LENGTH: 398
<212> TYPE: PRT
<213> ORGANISM: Unknown
<220> FEATURE:
<223> OTHER INFORMATION: Animal Stool
<220> FEATURE:
<221> NAME/KEY: PEPTIDE
<222> LOCATION: (1)..(398)

<400> SEQUENCE: 14

Ala Gln Ala Ala Ser Asp Ala Val Ile Asn Leu Asn Asn Thr His Gln
1               5                   10                  15

Glu Ile Met Gly Phe Gly Gly Met Asn His Pro Thr Trp Ala Gly Asp
                20                  25                  30

Leu Thr Ser Ser Gln Arg Glu Thr Ala Phe Gly Asn Gly Thr Asn Gln
            35                  40                  45
```

```
Leu Gly Phe Gln Val Leu Arg Ile Trp Val Asp Ser Asp Arg Asn Asn
 50                  55                  60

Trp Tyr Lys Glu Leu Ala Thr Ala Lys Ala Ala Leu Ala Lys Gly Ala
 65                  70                  75                  80

Ile Val Phe Ala Thr Pro Trp Asn Pro Pro Ser Asn Leu Cys Glu Thr
                     85                  90                  95

Phe Tyr Lys Asn Gly Ser Ala Asn Ala Lys Arg Leu Lys His Asp Lys
                    100                 105                 110

Tyr Ala Ala Tyr Ala Gln His Leu Asn Asp Phe Val Thr Tyr Met Arg
                115                 120                 125

Asn Asn Gly Val Glu Leu Tyr Gly Ile Ser Val Cys Asn Glu Pro Asp
130                 135                 140

Tyr Gly His Asp Trp Thr Trp Trp Thr Glu Ser Glu Val Val Thr Phe
145                 150                 155                 160

Leu Lys Tyr Tyr Ala Gly Ser Ile Asn Cys Arg Ile Ile Ala Pro Glu
                165                 170                 175

Ser Phe Ser Tyr Gln Lys Ser Tyr Tyr Asp Ala Ile Ile Asn Asp Ser
                180                 185                 190

Gln Ala Leu Ala Gln Val Asp Ile Ile Gly Thr His Leu Tyr Gly Thr
            195                 200                 205

Ser Tyr Asn Asn Phe Ser Tyr Pro Leu Tyr His Gln Lys Ala Ser Ser
210                 215                 220

Lys Gln Leu Trp Met Thr Glu Val Tyr Thr Pro Asn Ser Thr Ser Ser
225                 230                 235                 240

Ala Asp Lys Trp Pro Glu Ala Ile Asn Val Ala Glu His Ile His Lys
                245                 250                 255

Ala Met Val Asn Asp Phe Gln Thr Tyr Val Trp Trp Tyr Ile Arg Arg
                260                 265                 270

Ser Tyr Gly Pro Met Lys Glu Asp Gly Thr Leu Ser Lys Arg Gly Tyr
            275                 280                 285

Cys Met Ala Gln Phe Ser Lys Phe Ile Arg Arg Gly Tyr Lys Arg Val
        290                 295                 300

Asp Ala Thr Glu Asn Pro Asn Asn Gly Val Tyr Val Ser Ala Tyr Thr
305                 310                 315                 320

Gly Asp Gly Lys Ala Val Ile Val Ala Val Asn Ser Gly Ser Ser Asp
                325                 330                 335

Cys Ser Gln Ser Phe Thr Ile Lys Gly Lys Thr Leu Lys Asn Val Asp
                340                 345                 350

Arg Tyr Arg Thr Ser Gly Ser Glu Asn Leu Ala Lys Thr Ser Asn Leu
            355                 360                 365

Glu Leu Ser Gly Asn Gly Phe Trp Ala Tyr Leu Pro Ala Asn Ser Val
370                 375                 380

Ser Thr Phe Val Cys Thr Val Glu Asn Ser Ser Ser Asn Pro
385                 390                 395

<210> SEQ ID NO 15
<211> LENGTH: 382
<212> TYPE: PRT
<213> ORGANISM: Vibrio rhizosphaerae
<220> FEATURE:
<221> NAME/KEY: mat_peptide
<222> LOCATION: (1)..(382)

<400> SEQUENCE: 15

Gly Ser Val Tyr Ile Asn Phe Asn Thr Glu Tyr Gln Glu Ile Asp Gly
1                   5                  10                  15
```

Phe Gly Ala Met Asn Ala Pro Gly Trp Val Asn Asp Leu Thr Ser Ala
            20                  25                  30

Gln Ala Thr Lys Ala Phe Gly Asn Gly Asp Gly Gln Met Gly Leu Ser
        35                  40                  45

Ile Met Arg Met Arg Ile Asp Pro Asp Ser Asn Gln Trp Tyr Arg Gln
 50                  55                  60

Val Pro Thr Ala Gln Ile Ala Tyr Ser Tyr Gly Ala Lys Leu Leu Ala
 65                  70                  75                  80

Thr Pro Trp Ser Pro Pro Ala Tyr Met Lys Thr Asn Asn Asn Val Asn
                85                  90                  95

Asn Gly Gly Lys Leu Lys Lys Glu His Tyr Trp Gly Tyr Thr Asp His
                100                 105                 110

Leu Met Asp Phe Thr Asn Tyr Met Ala Gly Lys Asn Ala Pro Ile Tyr
            115                 120                 125

Ala Leu Ser Ile Gln Asn Glu Pro Asp Trp His Pro Asn Tyr Glu Ser
130                 135                 140

Cys Asp Trp Ser Gly Ala Asp Phe Val Asn Tyr Leu Asn Asp Gln Gly
145                 150                 155                 160

Trp Arg Leu Asp Ser Ser Leu Lys Ile Leu Ala Pro Glu Ser Leu Gly
                165                 170                 175

Phe Asn Pro Ala Leu Ser Asp Pro Ile Leu Lys Asp Ser Val Ala Ser
            180                 185                 190

Ser His Ile Asp Ile Ile Gly Gly His Leu Tyr Gly Val Gln Pro Arg
        195                 200                 205

Asn Tyr Pro Leu Ala Leu Gln Lys Gly Lys Lys Leu Trp Met Thr Glu
210                 215                 220

His Tyr Thr Asp Thr Asp Asn Ala Asn Ile Trp Asp Lys Ala Met Asn
225                 230                 235                 240

Val Gly Leu Glu Leu His Gln Ser Met Val Ser Asn Tyr Ser Ala Tyr
                245                 250                 255

Ile Trp Trp Tyr Leu Arg Arg Ser Tyr Gly Met Leu Thr Glu Asp Gly
            260                 265                 270

Asn Ile Ser Lys Arg Gly Tyr Ile Met Ser Gln Phe Ser Lys Phe Ile
        275                 280                 285

Arg Pro Gly Asp Val Arg Ile Ala Ala Thr Glu Val Pro Glu Ser Asn
290                 295                 300

Val Tyr Val Thr Ala Tyr Lys Asn Arg Ser Gly Lys Leu Val Ile Ala
305                 310                 315                 320

Val Val Asn Lys Thr Asn Ser His Lys Lys Leu Asp Phe Thr Leu Gln
                325                 330                 335

Asn Gly Thr Val Gly Ser Met Thr Lys Tyr Val Thr Ser Ala Ser Gln
            340                 345                 350

Asn Val Gly Tyr Ala Gly Lys Tyr Ala Val Ser Asn Asn Arg Phe Thr
        355                 360                 365

Ala Tyr Ala Asp Pro Leu Ser Val Gln Thr Phe Val Ser Glu
370                 375                 380

<210> SEQ ID NO 16
<211> LENGTH: 391
<212> TYPE: PRT
<213> ORGANISM: Bacillus subtilis
<220> FEATURE:
<221> NAME/KEY: PEPTIDE
<222> LOCATION: (1)..(391)

<400> SEQUENCE: 16

```
Ala Ala Ser Asp Val Thr Val Asn Val Ser Ala Glu Lys Gln Val Ile
1               5                   10                  15

Arg Gly Phe Gly Gly Met Asn His Pro Ala Trp Ala Gly Asp Leu Thr
            20                  25                  30

Ala Ala Gln Arg Glu Thr Ala Phe Gly Asn Gly Gln Asn Gln Leu Gly
        35                  40                  45

Phe Ser Ile Leu Arg Ile His Val Asp Glu Asn Arg Asn Asn Trp Tyr
    50                  55                  60

Lys Glu Val Glu Thr Ala Lys Ser Ala Val Lys His Gly Ala Ile Val
65                  70                  75                  80

Phe Ala Ser Pro Trp Asn Pro Pro Ser Asp Met Val Glu Thr Phe Asn
                85                  90                  95

Arg Asn Gly Asp Thr Ser Ala Lys Arg Leu Lys Tyr Asn Lys Tyr Ala
            100                 105                 110

Ala Tyr Ala Gln His Leu Asn Asp Phe Val Thr Phe Met Lys Asn Asn
        115                 120                 125

Gly Val Asn Leu Tyr Ala Ile Ser Val Gln Asn Glu Pro Asp Tyr Ala
    130                 135                 140

His Glu Trp Thr Trp Trp Thr Pro Gln Glu Ile Leu Arg Phe Met Arg
145                 150                 155                 160

Glu Asn Ala Gly Ser Ile Asn Ala Arg Val Ile Ala Pro Glu Ser Phe
                165                 170                 175

Gln Tyr Leu Lys Asn Leu Ser Asp Pro Ile Leu Asn Asp Pro Gln Ala
            180                 185                 190

Leu Ala Asn Met Asp Ile Leu Gly Thr His Leu Tyr Gly Thr Gln Val
        195                 200                 205

Ser Gln Phe Pro Tyr Pro Leu Phe Lys Gln Lys Gly Ala Gly Lys Asp
    210                 215                 220

Leu Trp Met Thr Glu Val Tyr Tyr Pro Asn Ser Asp Thr Asn Ser Ala
225                 230                 235                 240

Asp Arg Trp Pro Glu Ala Leu Asp Val Ser Gln His Ile His Asn Ala
                245                 250                 255

Met Val Glu Gly Asp Phe Gln Ala Tyr Val Trp Trp Tyr Ile Arg Arg
            260                 265                 270

Ser Tyr Gly Pro Met Lys Glu Asp Gly Thr Ile Ser Lys Arg Gly Tyr
        275                 280                 285

Asn Met Ala His Phe Ser Lys Phe Val Arg Pro Gly Tyr Val Arg Ile
    290                 295                 300

Asp Ala Thr Lys Asn Pro Asn Ala Asn Val Tyr Val Ser Ala Tyr Lys
305                 310                 315                 320

Gly Asp Asn Lys Val Val Ile Val Ala Ile Asn Lys Ser Asn Thr Gly
                325                 330                 335

Val Asn Gln Asn Phe Val Leu Gln Asn Gly Ser Ala Ser Asn Val Ser
            340                 345                 350

Arg Trp Ile Thr Ser Ser Ser Asn Leu Gln Pro Gly Thr Asn Leu
        355                 360                 365

Thr Val Ser Gly Asn His Phe Trp Ala His Leu Pro Ala Gln Ser Val
    370                 375                 380

Thr Thr Phe Val Val Asn Arg
385                 390
```

<210> SEQ ID NO 17

<211> LENGTH: 391
<212> TYPE: PRT
<213> ORGANISM: Bacillus amyloliquefaciens
<220> FEATURE:
<221> NAME/KEY: PEPTIDE
<222> LOCATION: (1)..(391)

<400> SEQUENCE: 17

Ala Ala Asn Asp Val Thr Val Asn Ile Ser Ala Glu Arg Gln Val Ile
1               5                   10                  15

Arg Gly Phe Gly Gly Met Asn His Pro Ala Trp Val Gly Asp Leu Thr
            20                  25                  30

Ala Ala Gln Arg Glu Thr Ala Phe Gly Asn Gly Gln Asn Gln Leu Gly
        35                  40                  45

Phe Ser Ile Leu Arg Ile His Val Asp Glu Asn Arg Asn Asn Trp Tyr
    50                  55                  60

Lys Glu Val Glu Thr Ala Lys Ser Ala Ile Lys His Gly Ala Ile Val
65                  70                  75                  80

Phe Ala Ser Pro Trp Asn Pro Pro Asn Asp Met Val Glu Thr Phe Asn
                85                  90                  95

His Asn Gly Asp Thr Ser Ala Lys Arg Leu Arg Tyr Asp Lys Tyr Ala
            100                 105                 110

Ala Tyr Ala Gln His Leu Asn Asp Phe Val Asn Phe Met Lys Ser Asn
        115                 120                 125

Gly Val Asn Leu Tyr Ala Ile Ser Ile Gln Asn Glu Pro Asp Tyr Ala
    130                 135                 140

His Glu Trp Thr Trp Trp Thr Pro Gln Glu Ile Leu Arg Phe Met Arg
145                 150                 155                 160

Glu Asn Ala Gly Ser Ile Asn Ala Arg Val Ile Ala Pro Glu Ser Phe
                165                 170                 175

Gln Tyr Leu Lys Asn Leu Ser Asp Pro Ile Leu Asn Asp Pro Gln Ala
            180                 185                 190

Leu Ala Asn Met Asp Ile Leu Gly Thr His Leu Tyr Gly Thr Gln Val
        195                 200                 205

Ser Gln Phe Pro Tyr Pro Leu Phe Lys Gln Lys Gly Ala Gly Lys Asp
    210                 215                 220

Leu Trp Met Thr Glu Val Tyr Tyr Pro Asn Ser Asp Asn Asn Ser Ala
225                 230                 235                 240

Asp Arg Trp Pro Glu Ala Leu Asp Val Ser Gln His Ile His Ser Ser
                245                 250                 255

Met Val Glu Gly Asp Leu Gln Ala Tyr Val Trp Trp Tyr Ile Arg Arg
            260                 265                 270

Ser Tyr Gly Pro Met Lys Glu Asp Gly Thr Ile Ser Lys Arg Gly Tyr
        275                 280                 285

Asn Met Ala His Phe Ser Lys Phe Val Arg Pro Gly Tyr Val Arg Ile
    290                 295                 300

Asp Ala Thr Lys Asn Pro Asn Pro Asn Val Tyr Val Ser Ala Tyr Lys
305                 310                 315                 320

Gly Asp Asn Lys Val Val Ile Val Ala Ile Asn Lys Thr Asn Thr Gly
                325                 330                 335

Val Asn Gln Asn Phe Val Leu Gln Asn Gly Ser Ala Ser Gln Val Ser
            340                 345                 350

Arg Trp Ile Thr Ser Ser Asn Ser Asn Leu Gln Pro Gly Thr Asp Leu
        355                 360                 365

Lys Val Thr Asp Asn His Phe Trp Ala His Leu Pro Ala Gln Ser Val

```
                    370                 375                 380
Thr Thr Phe Val Val Lys Arg
385                 390

<210> SEQ ID NO 18
<211> LENGTH: 392
<212> TYPE: PRT
<213> ORGANISM: Bacillus licheniformis
<220> FEATURE:
<221> NAME/KEY: PEPTIDE
<222> LOCATION: (1)..(392)

<400> SEQUENCE: 18

Ala Ala Ser Asp Ala Thr Val Arg Leu Ser Ala Glu Lys Gln Val Ile
1               5                   10                  15

Arg Gly Phe Gly Gly Met Asn His Pro Ala Trp Ile Gly Asp Leu Thr
                20                  25                  30

Ala Ala Gln Arg Glu Thr Ala Phe Gly Asn Gly Gln Asn Gln Leu Gly
            35                  40                  45

Phe Ser Ile Leu Arg Ile His Val Asp Glu Asn Arg Asn Asn Trp Tyr
    50                  55                  60

Arg Glu Val Glu Thr Ala Lys Ser Ala Ile Lys His Gly Ala Ile Val
65                  70                  75                  80

Phe Ala Ser Pro Trp Asn Pro Pro Ser Asp Met Val Glu Thr Phe Asn
                85                  90                  95

Arg Asn Gly Asp Thr Ser Ala Lys Arg Leu Arg Tyr Asp Lys Tyr Ala
                100                 105                 110

Ala Tyr Ala Lys His Leu Asn Asp Phe Val Thr Phe Met Lys Asn Asn
            115                 120                 125

Gly Val Asn Leu Tyr Ala Ile Ser Val Gln Asn Glu Pro Asp Tyr Ala
        130                 135                 140

His Asp Trp Thr Trp Trp Thr Pro Gln Glu Ile Leu Arg Phe Met Lys
145                 150                 155                 160

Glu Asn Ala Gly Ser Ile Asn Ala Arg Val Ile Ala Pro Glu Ser Phe
                165                 170                 175

Gln Tyr Leu Lys Asn Ile Ser Asp Pro Ile Val Asn Asp Pro Lys Ala
            180                 185                 190

Leu Ala Asn Met Asp Ile Leu Gly Ala His Leu Tyr Gly Thr Gln Leu
        195                 200                 205

Asn Asn Phe Ala Tyr Pro Leu Phe Lys Gln Lys Gly Ala Gly Lys Asp
    210                 215                 220

Leu Trp Met Thr Glu Val Tyr Tyr Pro Asn Ser Asp Asn His Ser Ala
225                 230                 235                 240

Asp Arg Trp Pro Glu Ala Leu Asp Val Ser His His Ile His Asn Ser
                245                 250                 255

Met Val Glu Gly Asp Phe Gln Ala Tyr Val Trp Trp Tyr Ile Arg Arg
            260                 265                 270

Ser Tyr Gly Pro Met Lys Glu Asp Gly Thr Ile Ser Lys Arg Gly Tyr
        275                 280                 285

Asn Met Ala His Phe Ser Lys Phe Val Arg Pro Gly Tyr Val Arg Val
    290                 295                 300

Asp Ala Thr Lys Ser Pro Ala Ser Asn Val Tyr Val Ser Ala Tyr Lys
305                 310                 315                 320

Gly Asp Asn Lys Val Val Ile Val Ala Ile Asn Lys Asn Asn Ser Gly
                325                 330                 335
```

```
Val Asn Gln Asn Phe Val Leu Gln Asn Gly Ser Val Ser Gln Val Ser
            340                 345                 350

Arg Trp Ile Thr Ser Ser Ser Asn Leu Gln Pro Gly Thr Asn Leu
        355                 360                 365

Asn Val Thr Asp Asn His Phe Trp Ala His Leu Pro Ala Gln Ser Val
    370                 375                 380

Thr Thr Phe Val Ala Asn Leu Arg
385                 390

<210> SEQ ID NO 19
<211> LENGTH: 391
<212> TYPE: PRT
<213> ORGANISM: Bacillus subtilis
<220> FEATURE:
<221> NAME/KEY: PEPTIDE
<222> LOCATION: (1)..(391)

<400> SEQUENCE: 19

Ala Ala Asn Asp Val Thr Val Asn Ile Ser Ala Glu Lys Gln Val Ile
1               5                   10                  15

Arg Gly Phe Gly Gly Met Asn His Pro Ala Trp Val Gly Asp Leu Thr
            20                  25                  30

Ala Ala Gln Arg Glu Thr Ala Phe Gly Asn Gly Gln Asn Gln Leu Gly
        35                  40                  45

Phe Ser Ile Leu Arg Ile His Val Asp Glu Asn Arg Asn Asn Trp Tyr
50                  55                  60

Lys Glu Val Glu Thr Ala Lys Ser Ala Ile Lys His Gly Ala Ile Val
65                  70                  75                  80

Phe Ala Ser Pro Trp Asn Pro Pro Ser Asn Met Val Glu Thr Phe Asn
                85                  90                  95

His Asn Gly Asp Thr Ser Ala Lys Arg Leu Arg Tyr Asp Lys Tyr Ala
            100                 105                 110

Ala Tyr Ala Gln His Leu Asn Asp Phe Val Thr Phe Met Lys Ser Asn
        115                 120                 125

Gly Val Asn Leu Tyr Ala Ile Ser Ile Gln Asn Glu Pro Asp Tyr Ala
    130                 135                 140

His Glu Trp Thr Trp Trp Thr Pro Gln Glu Ile Leu Arg Phe Met Arg
145                 150                 155                 160

Glu Asn Ala Gly Ser Ile Asn Ala Arg Val Ile Ala Pro Glu Ser Phe
                165                 170                 175

Gln Tyr Leu Lys Asn Leu Ser Asp Pro Ile Leu Asn Asp Pro Gln Ala
            180                 185                 190

Leu Ala Asn Met Asp Ile Leu Gly Thr His Leu Tyr Gly Thr Gln Val
        195                 200                 205

Ser Gln Phe Pro Tyr Pro Leu Phe Lys Gln Lys Gly Ala Gly Lys Asp
    210                 215                 220

Leu Trp Met Thr Glu Val Tyr Tyr Pro Asn Ser Asp Asn Asn Ser Ala
225                 230                 235                 240

Asp Arg Trp Pro Glu Ala Leu Asp Val Ser Gln His Ile His Asn Ser
                245                 250                 255

Met Val Glu Gly Asp Phe Gln Ala Tyr Val Trp Trp Tyr Ile Arg Arg
            260                 265                 270

Ser Tyr Gly Pro Met Lys Glu Asp Gly Thr Ile Ser Lys Arg Gly Tyr
        275                 280                 285

Asn Met Ala His Phe Ser Lys Phe Val Arg Pro Gly Tyr Val Arg Ile
    290                 295                 300
```

-continued

```
Asp Ala Thr Lys Asn Pro Asn Pro Asn Val Tyr Val Ser Ala Tyr Lys
305                 310                 315                 320

Gly Asp Asn Lys Val Val Ile Val Ala Ile Asn Lys Ser Asn Thr Gly
                325                 330                 335

Val Asn Gln Asn Phe Val Leu Gln Asn Gly Ser Ala Ser Gln Val Ser
            340                 345                 350

Arg Trp Ile Thr Ser Ser Asn Ser Asn Leu Gln Pro Gly Thr Asn Leu
        355                 360                 365

Lys Val Thr Asp Asn His Phe Trp Ala His Leu Pro Ala Gln Ser Val
370                 375                 380

Thr Thr Phe Val Val Ile Arg
385                 390

<210> SEQ ID NO 20
<211> LENGTH: 393
<212> TYPE: PRT
<213> ORGANISM: Paenibacillus pabuli
<220> FEATURE:
<221> NAME/KEY: PEPTIDE
<222> LOCATION: (1)..(393)

<400> SEQUENCE: 20

Ala Ala Ser Asp Val Thr Val Asn Leu Ser Ser Glu Lys Gln Leu Ile
1               5                   10                  15

Lys Gly Phe Gly Gly Ile Asn His Pro Asn Trp Ile Gly Asp Leu Thr
            20                  25                  30

Pro Ser Gln Arg Asp Thr Ala Phe Gly Asn Gly Gln Asn Gln Leu Gly
        35                  40                  45

Phe Ser Ile Leu Arg Ile Tyr Ile Asp Asp Asn Lys Asn Asn Trp Tyr
    50                  55                  60

Lys Glu Ile Pro Thr Ala Lys Arg Ala Ile Glu Gln Gly Ala Ile Val
65                  70                  75                  80

Phe Ala Ser Pro Trp Asn Pro Pro Ser Asp Met Val Glu Thr Phe Asn
                85                  90                  95

Arg Asn Gly Asp Thr Ala Ala Lys Arg Leu Lys Tyr Asp Lys Tyr Ala
            100                 105                 110

Ala Tyr Ala Gln His Leu Asn Asp Phe Val Ser Tyr Met Lys Ser Asn
        115                 120                 125

Gly Val Asn Leu Tyr Ala Ile Ser Val Gln Asn Glu Pro Asp Tyr Ala
    130                 135                 140

His Asp Trp Thr Trp Trp Thr Pro Gln Glu Met Leu Arg Phe Met Lys
145                 150                 155                 160

Asp Tyr Ala Gly Ser Ile Thr Gly Thr Lys Val Met Ala Pro Glu Ser
                165                 170                 175

Phe Ser Tyr Leu Lys Glu Met Ser Asp Pro Ile Leu Asn Asp Pro Gln
            180                 185                 190

Ala Leu Ala Asn Met Asp Ile Leu Gly Ala His Thr Tyr Gly Thr Gln
        195                 200                 205

Phe Ser Asn Phe Pro Tyr Pro Leu Phe Lys Gln Lys Gly Ala Gly Lys
    210                 215                 220

Glu Leu Trp Met Ser Glu Val Tyr Tyr Pro Asn Ser Asn Ala Asn Ser
225                 230                 235                 240

Ala Asp His Trp Pro Glu Ala Leu Asp Val Ser Tyr His Ile His His
                245                 250                 255

Ala Met Val Glu Ala Asp Phe Gln Ala Tyr Val Trp Trp Tyr Ile Arg
```

```
                260                 265                 270
Arg Gln Tyr Gly Pro Met Lys Glu Asp Gly Thr Ile Ser Lys Arg Gly
            275                 280                 285

Tyr Asn Met Ala His Phe Ser Lys Phe Val Arg Pro Gly Phe Val Arg
        290                 295                 300

Val Asp Ala Thr Lys Asn Pro Asp Thr Gln Thr Phe Ile Ser Ala Phe
305                 310                 315                 320

Lys Gly Asp Asn Lys Val Val Ile Val Ala Ile Asn Arg Gly Thr Ser
                325                 330                 335

Ala Val Asn Gln Lys Phe Val Leu Gln Asn Gly Asn Ala Ser Asn Val
            340                 345                 350

Ser Ser Trp Val Thr Asp Ser Thr Arg Asn Leu Ala Ala Gly Ser Ser
        355                 360                 365

Ile Ile Met Thr Gly Asn Thr Phe Thr Ala Gln Leu Pro Ser Gln Ser
370                 375                 380

Val Thr Thr Phe Val Ala Gln Leu Asn
385                 390
```

<210> SEQ ID NO 21
<211> LENGTH: 391
<212> TYPE: PRT
<213> ORGANISM: Bacillus amyloliquefaciens
<220> FEATURE:
<221> NAME/KEY: PEPTIDE
<222> LOCATION: (1)..(391)

<400> SEQUENCE: 21

```
Ala Ala Ser Asp Ala Thr Val Asn Ile Ser Ala Glu Arg Gln Val Ile
1               5                   10                  15

Arg Gly Phe Gly Gly Met Asn His Pro Ala Trp Ile Gly Asp Leu Thr
            20                  25                  30

Ala Pro Gln Arg Val Thr Ala Phe Gly Asn Gly Gln Asn Gln Leu Gly
        35                  40                  45

Phe Ser Val Leu Arg Ile His Val Asp Glu Asn Arg Asn Asn Trp Tyr
    50                  55                  60

Lys Glu Val Glu Thr Ala Lys Ser Ala Ile Lys His Gly Ala Ile Val
65                  70                  75                  80

Phe Ala Ser Pro Trp Asn Pro Pro Asn Asp Met Val Glu Thr Phe Asn
                85                  90                  95

His Asn Gly Asp Thr Ser Ala Lys Arg Leu Arg Tyr Asp Lys Tyr Ala
            100                 105                 110

Ala Tyr Ala Gln His Leu Asn Asp Phe Val Asn Phe Met Lys Ser Asn
        115                 120                 125

Gly Val Asn Leu Tyr Ala Ile Ser Met Gln Asn Glu Pro Asp Tyr Ala
    130                 135                 140

His Glu Trp Thr Trp Trp Thr Pro Gln Glu Ile Leu Arg Phe Met Arg
145                 150                 155                 160

Glu Asn Ala Gly Ser Ile Asn Thr Arg Val Ile Ala Pro Glu Ser Phe
                165                 170                 175

Gln Tyr Leu Lys Asn Ile Ser Asp Pro Ile Leu Asn Asp Pro Gln Ala
            180                 185                 190

Leu Arg Asn Met Asp Ile Leu Gly Thr His Leu Tyr Gly Thr Gln Val
        195                 200                 205

Ser Gln Phe Pro Tyr Pro Leu Phe Lys Gln Lys Gly Gly Gly Lys Glu
    210                 215                 220
```

```
Leu Trp Met Thr Glu Val Tyr Tyr Pro Asn Ser Asp Asn Tyr Ser Ala
225             230                 235                 240

Asp Arg Trp Pro Glu Ala Leu Gly Val Ser Glu His Ile His His Ser
            245                 250             255

Met Val Glu Gly Asp Phe Gln Ala Tyr Val Trp Trp Tyr Ile Arg Arg
            260                 265                 270

Ser Tyr Gly Pro Met Lys Glu Asp Gly Met Ile Ser Lys Arg Gly Tyr
        275             280                 285

Asn Met Ala His Phe Ser Lys Phe Val Arg Pro Gly Tyr Val Arg Ile
        290             295                 300

Asp Ala Thr Lys Asn Pro Glu Pro Asn Val Tyr Val Ser Ala Tyr Lys
305             310                 315                 320

Gly Asp Asn Lys Val Val Ile Val Ala Ile Asn Lys Asn Asn Thr Gly
                325                 330                 335

Val Asn Gln Asn Phe Val Leu Gln Asn Gly Thr Ala Ser Gln Val Ser
                340                 345                 350

Arg Trp Ile Thr Ser Ser Ser Asn Leu Gln Pro Gly Thr Asp Leu
            355                 360                 365

Lys Val Thr Asp Asn His Phe Trp Ala His Leu Pro Ala Gln Ser Val
        370                 375                 380

Thr Thr Phe Val Val Lys Arg
385                 390
```